US008835613B2

(12) United States Patent  
Berzofsky et al.

(10) Patent No.: US 8,835,613 B2  
(45) Date of Patent: Sep. 16, 2014

(54) β-MANNOSYLCERAMIDE AND STIMULATION OF NKT CELL ANTI-TUMOR IMMUNITY

(75) Inventors: Jay A. Berzofsky, Bethesda, MD (US); Jessica J. O'Konek, Ann Arbor, MI (US); Masaki Terabe, Bethesda, MD (US); Petr Illarionov, Birmingham (GB); Gurdyal S. Besra, Solihull (GB)

(73) Assignees: The United States of America, as represented by the Secretary, Department of Health and Human Services, Washington, DC (US); The University of Birmingham, of Edgbaston, Birmingham (GB)

( * ) Notice: Subject to any disclaimer, the term of this patent is extended or adjusted under 35 U.S.C. 154(b) by 0 days.

(21) Appl. No.: 13/582,612

(22) PCT Filed: Mar. 11, 2011

(86) PCT No.: PCT/US2011/028024  
§ 371 (c)(1),  
(2), (4) Date: Oct. 2, 2012

(87) PCT Pub. No.: WO2011/112889  
PCT Pub. Date: Sep. 15, 2011

(65) Prior Publication Data  
US 2013/0039886 A1 Feb. 14, 2013

Related U.S. Application Data

(60) Provisional application No. 61/313,508, filed on Mar. 12, 2010.

(51) Int. Cl.  
*A61K 31/7032* (2006.01)  
*A61K 38/19* (2006.01)  
*A61K 39/00* (2006.01)  
*A61K 38/20* (2006.01)  
*A61K 39/395* (2006.01)  
*C07H 15/04* (2006.01)  
*A61P 37/04* (2006.01)  
*A61K 31/7004* (2006.01)

(52) U.S. Cl.  
CPC .................. *A61K 31/7004* (2013.01)  
USPC ........................ 536/17.9; 424/85.2

(58) Field of Classification Search  
USPC .......................... 424/85.2; 536/17.9  
See application file for complete search history.

(56) References Cited

U.S. PATENT DOCUMENTS

| | | | |
|---|---|---|---|
| 6,531,453 B1 | 3/2003 | Taniguchi et al. | |
| 6,747,010 B2 | 6/2004 | Taniguchi et al. | |
| 2004/0248915 A1* | 12/2004 | Jolivet et al. | 514/269 |
| 2005/0112141 A1 | 5/2005 | Terman | |
| 2006/0216316 A1 | 9/2006 | Dhodapkar et al. | |
| 2008/0254045 A1 | 10/2008 | Donda et al. | |
| 2009/0047299 A1 | 2/2009 | Savage et al. | |

FOREIGN PATENT DOCUMENTS

| | | | | |
|---|---|---|---|---|
| WO | WO 2005/014008 A2 * | 2/2005 | ............ | A61K 31/70 |
| WO | WO 2006/026389 A2 * | 3/2006 | | |
| WO | WO 2007/050668 A1 * | 5/2007 | ............ | A61K 35/28 |
| WO | WO 2008/133801 A1 | 11/2008 | | |

OTHER PUBLICATIONS

The Merck Manual, 1992, pp. 1263, 166-67 and 1268-69.*  
Trisha Gura, Science, Nov., 1997, pp. 1041-42.*  
Seventer, G.A.V. et al J. Immunology, 1990, 144(12), 4579-586.*  
Berzofsky et al., "Novel Agonist of Mouse and Human iNKT Cells Reveals a New Mechanism of Tumor Immunity," *NCI Intramural Scientific Investigators Retreat*, Abstract #138, 70 (2011).  
Coste et al., "IL-13 attenuates gastrointestinal candidiasis in normal and immunodeficient RAG-2$^{-/-}$ mice via peroxisome proliferator-activated receptor-γ activation," *J. Immunol.*, 180 (7), 4939-4947 (2008).  
Dalpozzo et al., "Simple and efficient chemoselective mild deprotection of acetals and ketals using cerium(III) triflate," *J. Org. Chem.*, 67 (25), 9093-9095 (2002).  
Fichtner-Feigl et al., "Restoration of tumor immunosurveillance via targeting of interleukin-13 receptor-α$_2$," *Cancer Res.*, 68 (9), 3467-3475 (2008).  
Forestier et al., "Improved outcomes in NOD mice treated with a novel Th2 cytokine-biasing NKT cell activator," *J. Immunol.*, 178 (3), 1415-1425 (2007).  
Gumperz et al., "Murine CD1d-restricted T cell recognition of cellular lipids," *Immunity*, 12 (2), 211-221 (2000).  
Hodosi et al., "A Fundamentally New, Simple, Stereospecific Synthesis of Oligosaccharides Containing the β-Mannopyranosyl and β-Rhamnopyranosyl Linkage," *J. Am. Chem. Soc.*, 119 (9), 2335-2336 (1997).  
International Search Report, Application No. PCT/US2011/028024, dated Jun. 9, 2011.  
Ndonye et al., "Synthesis and evaluation of sphinganine analogues of KRN7000 and OCH," *J. Org. Chem.*, 70 (25), 10260-10270 (2005).  
Okamoto et al., "Synthetic α-mannosyl Ceramide as a Potent Stimulant for an NKT Cell Repertoire Bearing the Invariant Vα19-Jα26 TCR α Chain," *Chem. Biol.*, 12, 677-683 (2005).  
O'Konek, et al., "Mouse and human iNKT cell agonist β-mannosylceramide reveals a distinct mechanism of tumor immunity", *J. Clin. Invest.*, 121 (2), 683-694 (2011).  
Park et al., "Unmasking immunosurveillance against a syngeneic colon cancer by elimination of CD4$^+$NKT regulatory cells and IL-13," *Int. J. Cancer*, 114 (1), 80-87 (2004).  
PowerPoint presentation and abstract relating to the invention, presented at the 5th International Symposium on CD1 and NKT cells, in Kamakura, Japan, on Mar. 23-27, 2009.

(Continued)

*Primary Examiner* — Ganapathy Krishnan  
(74) *Attorney, Agent, or Firm* — Leydig, Voit & Mayer

(57) ABSTRACT

β-mannosylceramides or salts or solvates thereof in a pharmaceutically acceptable carrier, for use as a Type I NKT cell agonist in conjunction with a therapeutically effective amount of α-galactosylceramide or a salt or a solvate thereof, and/or at least one or more T-cell co-stimulatory molecules, disclosed. Compositions comprising β-mannosylceramide, as well as methods of treatment of tumors are also provided.

24 Claims, 14 Drawing Sheets

(56) References Cited

OTHER PUBLICATIONS

Schmidt et al., "Synthesis of Glycosphingolipids and Psychosines," *Angew. Chem. Int. Ed. Engl.*, 25 (8), 725-726 (1986).

Schümann et al., "MR1-restricted Vα19i T cells-a second population recognizing lipid antigens?" *Eur. J. Immunol.*, 37 (7), 1724-1726 (2007).

Terabe, "Regulation of Tumor Immunity by Natural Killer T-cell Subsets", *J. Immunother*, 32 (9), 1000 (2009).

Van Den Berg et al., "A simple and low cost synthesis of d-erythro-sphingosine and d-erythro-azidosphingosine from d-ribo-phytosphingosine: glycosphingolipid precursors," *Tetrahedron Letters*, 43 (46), 8409-8412 (2002).

Yu et al., "Modulation of CD1d-restricted NKT cell responses by using *N*-acyl variants of α-galactosylceramides," *Proc Natl. Acad. Sci. U S A*, 102 (9), 3383-3388 (2005).

* cited by examiner

A

B

C

A

B

DONOR A

DONOR B

β-MANNOSYLCERAMIDE AND STIMULATION OF NKT CELL ANTI-TUMOR IMMUNITY

CROSS-REFERENCE TO RELATED APPLICATION

This application is the U.S. national phase of International Patent Application No. PCT/US2011/028024, filed Mar. 11, 2011, which claims the benefit of U.S. Provisional Patent Application No. 61/313,508, filed Mar. 12, 2010, the entire contents of each of which are incorporated herein by reference.

BACKGROUND OF THE INVENTION

Natural killer T cells (NKT) are a unique lymphocyte population that expresses a T cell receptor (TCR) as well as NK lineage markers and possesses functional properties of both T and NK cells. Type I NKT cells, often called invariant NKT (iNKT) cells, express an invariant TCRα chain composed of a Vα14-Jα18 chain rearrangement in mice (Vα24-Jα18 in humans), that pairs preferentially with Vβ8.2, 7, and 2 (Vβ11 in humans). NKT cells are defined functionally by their ability to recognize glycolipid antigens presented in the context of the MHC class Ib molecule CD1d. NKT cells bridge the gap between the innate and adaptive immune systems and are equipped to rapidly respond to stimuli to elicit an immune response.

When activated, iNKT cells rapidly produce large amounts of cytokines including interferon-γ (IFN-γ), IL-4 and IL-13, and the cytokine profile differs depending on the stimulus. α-galactosylceramide (α-GalCer) is the most extensively studied ligand for CD1d and is well established to be a potent stimulator of iNKT cells in both mice and humans. α-GalCer-stimulated iNKT cells produce high levels of IFN-γ and promote immunity against tumors as well as infectious pathogens. Multiple studies in murine tumor models have shown the ability of α-GalCer to induce anti-tumor immunity by iNKT- and IFN-γ-dependent mechanisms.

There still exists a need in the art to develop methods of NKT cell activation which may result in other ways to treat certain cancers, or induce immune responses.

BRIEF SUMMARY OF THE INVENTION

In an embodiment, the present invention provides compositions for activating NKT cells in a mammal comprising a β-mannosylceramide (β-ManCer) or a salt or solvate thereof in a pharmaceutically acceptable carrier.

In another embodiment, the present invention provides compositions for activating NKT cells in a mammal, the compositions comprising a β-mannosylceramide (β-ManCer) or a salt or solvate thereof in a pharmaceutically acceptable carrier, wherein the β-ManCer comprises a sphingosine moiety and a fatty acid moiety comprising a linear or branched, saturated or unsaturated, aliphatic hydrocarbon group having from about 8 to about 49 carbon atoms. In another embodiment, the fatty acid moiety can comprise a linear or branched, saturated or unsaturated, aliphatic hydrocarbon group having from about 18 to about 49 carbon atoms. In other embodiments, the fatty acid moiety can comprise a linear or branched, saturated or unsaturated, aliphatic hydrocarbon group having from about 8 to about 15 carbon atoms. In another embodiment, the fatty acid moiety can comprise a linear or branched, saturated or unsaturated, aliphatic hydrocarbon group having from about 18 to about 30 carbon atoms.

In yet another embodiment, the present invention provides compositions for activating NKT cells in a mammal, the compositions comprising a β-mannosylceramide (β-ManCer) or a salt or solvate thereof in a pharmaceutically acceptable carrier, wherein the β-ManCer has the following structure:

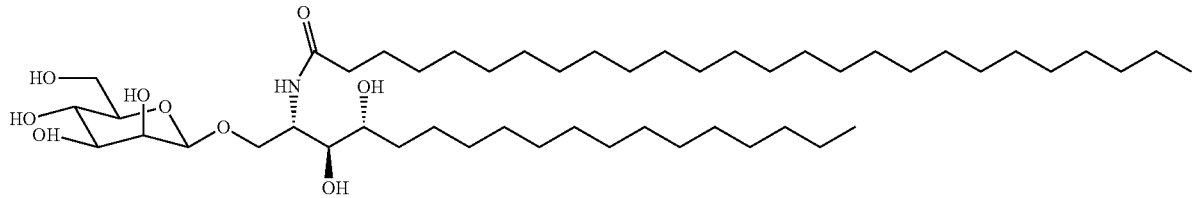 [SMILES: CCCCCCCCCCCCCCCCCCCCCCCCCC(=O)N[C@@H](COC1OC(CO)C(O)C(O)C1O)[C@H](O)[C@H](O)CCCCCCCCCCCCCC]

The compositions described can also include other immunostimulatory compounds. In an embodiment, the above compositions can also comprise a therapeutically effective amount of IL-2, and/or granulocyte/macrophage colony-stimulating factor (GM-CSF), and/or other cytokines that induce cellular immunity such as IL-12 and/or IL-15.

In a further embodiment, the present invention provides compositions for activating NKT cells in a mammal the compositions comprising a β-ManCer or a salt or solvate thereof, and a therapeutically effective amount of an α-glycosylceramide, or a salt or solvate thereof. The α-glycosylceramide, in an embodiment, can be an α-galactosylceramide.

In an embodiment, the present invention provides a method for activating NKT cells in a mammal comprising administering to the mammal, a therapeutically effective amount of a pharmaceutical composition comprising β-ManCer, or a salt or solvate thereof.

In a further embodiment, the present invention provides a composition comprising a therapeutically effective amount of a pharmaceutical composition comprising β-ManCer, or a salt or solvate thereof, and a therapeutically effective amount of at least one or more T-cell co-stimulatory molecules or Toll-like receptor (TLR) ligands.

In an embodiment, the present invention also provides methods for activating NKT cells in a mammal. In particular, the present invention provides a method for activating NKT cells in a mammal comprising administering to the mammal, a therapeutically effective amount of a pharmaceutical composition comprising β-ManCer, or a salt or solvate thereof, and a therapeutically effective amount of IL-2.

In yet another embodiment, the present invention provides a method for activating NKT cells in a mammal comprising administering to the mammal, a therapeutically effective amount of a pharmaceutical composition comprising β-ManCer, or a salt or solvate thereof, and a therapeutically effective amount of α-GalCer.

In a further embodiment, the present invention provides a method for activating NKT cells in a mammal comprising administering to the mammal, a therapeutically effective amount of a pharmaceutical composition comprising a therapeutically effective amount of: (i) β-ManCer, or a salt or a solvate thereof; (ii) GM-CSF; and (iii) other cytokines that induce cellular immunity, such as IL-12 and/or IL-15.

In another embodiment, a method for activating NKT cells in a mammal comprises administering to the mammal, a therapeutically effective amount of a pharmaceutical composition comprising β-ManCer, or a salt or solvate thereof, and a therapeutically effective amount of an α-glycosylceramide, or a salt or solvate thereof. The method can also encompass a method for activating NKT cells in a mammal comprising administering to the mammal, a therapeutically effective amount of a pharmaceutical composition comprising β-ManCer, or a salt or solvate thereof, and a therapeutically effective amount of at least one or more T-cell co-stimulatory molecules, or TLR ligands.

In another embodiment, the present invention provides a method of treating or inhibiting the growth of tumor in a subject comprising administering to the subject a therapeutically effective amount of the pharmaceutical composition of β-ManCer, or a salt or solvate thereof, either as a monotherapy, or in conjunction with a therapeutically effective amount of an α-glycosylceramide, or a salt or solvate thereof, and/or at least one or more T-cell co-stimulatory molecules, or TLR ligands.

In another embodiment, the present invention provides a method of treating or inhibiting cancer in a subject comprising administering to the subject a therapeutically effective amount of the pharmaceutical composition of β-ManCer or a salt or solvate thereof, either as a monotherapy, or in conjunction with a therapeutically effective amount of an α-glycosylceramide or a salt or solvate thereof, and/or at least one or more T-cell co-stimulatory molecules, or TLR ligands.

In an embodiment, the present invention provides a method for inducing an immune response in a subject comprising administering to the subject a therapeutically effective amount of the pharmaceutical composition of β-ManCer, or a salt or solvate thereof, in conjunction with one or more antibodies, including, for example, antibodies against CTLA-4 or PD-1 or TGF-beta.

In a further embodiment, the present invention provides a method for inducing an immune response in a subject comprising administering to the subject a therapeutically effective amount of the pharmaceutical composition of β-ManCer, or a salt or solvate thereof, in conjunction with a vaccine, for example, such as a TARP 29-37-9V and an effective amount of the pharmaceutical composition of β-ManCer, or a salt or solvate thereof.

In another embodiment, the present invention provides a method for inducing an immune response in a subject comprising contacting peripheral blood mononuclear cells of a subject in vitro, together with a vaccine, for example, such as a TARP 29-37-9V and an effective amount of the pharmaceutical composition of β-ManCer, or a salt or solvate thereof, and incubating the monocyte-derived dendritic cells made from patients' peripheral blood mononuclear cells together with the vaccine for a period of time, followed by administration of the cells into the subject.

It is also contemplated that NKT cells of a subject are activated in vitro, and subsequently administered to the subject for use in the treatment or inhibition of the growth of a tumor, or cancer in the subject. In particular, in an embodiment, the present invention provides a method of treating or inhibiting the growth of a tumor or neoplasm in a subject comprising administering to the subject an effective amount of activated NKT cells which were derived from culturing in vitro a mononuclear cell fraction, the cell fraction comprising one or more NKT cells in the presence of β-ManCer, or a salt or solvate thereof, and optionally, an α-glycosylceramide, or a salt or solvate thereof. The method of treatment of a tumor can also encompass culturing in vitro, a mononuclear cell fraction, the cell fraction comprising a one or more NKT cells in the presence of β-ManCer, or a salt or solvate thereof, and optionally, an α-glycosylceramide, or a salt or solvate thereof, and at least one or more T-cell co-stimulatory molecules, or TLR ligands.

BRIEF DESCRIPTION OF THE SEVERAL VIEWS OF THE DRAWING(S)

FIG. 1 shows an example of an embodiment of the present invention. The chemical structures of the particular β-ManCer, α-GalCer, α-ManCer, and α-FucCer glycolipids used in the examples are provided.

FIG. 2A shows β-ManCer, but not α-ManCer, or α-FucCer, induced strong protection against CT26 lung metastasis in an iNKT cell-dependent manner. CT26 cells ($5 \times 10^5$) were injected i.v. into the tail vein of BALB/c mice and glycolipids administered within one hour after tumor challenge. Mice were sacrificed 14-16 days after tumor challenge and lung metastases were enumerated. Mice were treated with vehicle (filled diamonds), α-FucCer (open circles), α-ManCer (open squares), 50 pmoles β-ManCer (filled squares), or 50 pmoles α-GalCer (filled triangles).

FIG. 2B is a graph depicting that β-ManCer was not inducing tumor protection by a mechanism independent of iNKT cells, by measuring its ability to protect in Jα18KO mice, which lack only iNKT cells. All protection was lost in Jα18KO mice, confirming that β-ManCer is iNKT-specific. WT (filled symbols) or Jα18$^{-/-}$ (open symbols) mice were treated with vehicle (circles) or β-ManCer (squares).

FIG. 2C is a graph showing that inhibition of peroxisome proliferator-activated receptor-γ (PPARγ), a transcription factor that regulates mannose receptor expression, with the irreversible inhibitor GW 9662, had no effect on β-ManCer-induced protection. This supports the finding that protection induced by β-ManCer is completely dependent on type I NKT cells, and is not due to signaling through the mannose receptor. 0.15 mg/ml GW9662 (200 μL i.p.) (PPARγ inhibitor; open symbols) or vehicle control (0.5% DMSO in PBS; filled symbols) was administered immediately following tumor challenge, and then 30 minutes prior to administration of 50 pmoles glycolipid or vehicle.

FIG. 2D compares the activity of β-ManCer to that of α-GalCer, as well as two previously described α-GalCer analogs, C20:2 and OCH, known to activate iNKT cells but induce cytokine profiles more skewed towards a Th2 response. A rank order of tumor protection was established at a dose of 50 pmoles, α-GalCer induced the greatest protection, followed by β-ManCer and C20:2, which were similarly protective. AH04-2 and OCH induced significantly less tumor killing. Mice were treated with 50 pmoles (filled symbols) or 5 pmoles (open symbols) of α-GalCer (triangles), β-ManCer (squares), C20:2 (circles), AH04-2 (diamonds), or OCH (inverted triangles). (*, statistically significant from vehicle control, $p<0.05$)

FIG. 3 is a series of graphs showing how β-ManCer also induced proliferation of 40% of iNKT cells, as measured by CFSE dilution after a 3.5-day stimulation, comparable to α-GalCer, which induced proliferation of 44% of iNKT cells, and this proliferation was inhibited to 5.4% (86% inhibition) with a CD1d-blocking antibody, confirming that iNKT cells recognize β-ManCer in the context of CD1d (Vehicle (3A), α-GalCer (3B), β-ManCer (3C)).

Figure 7:
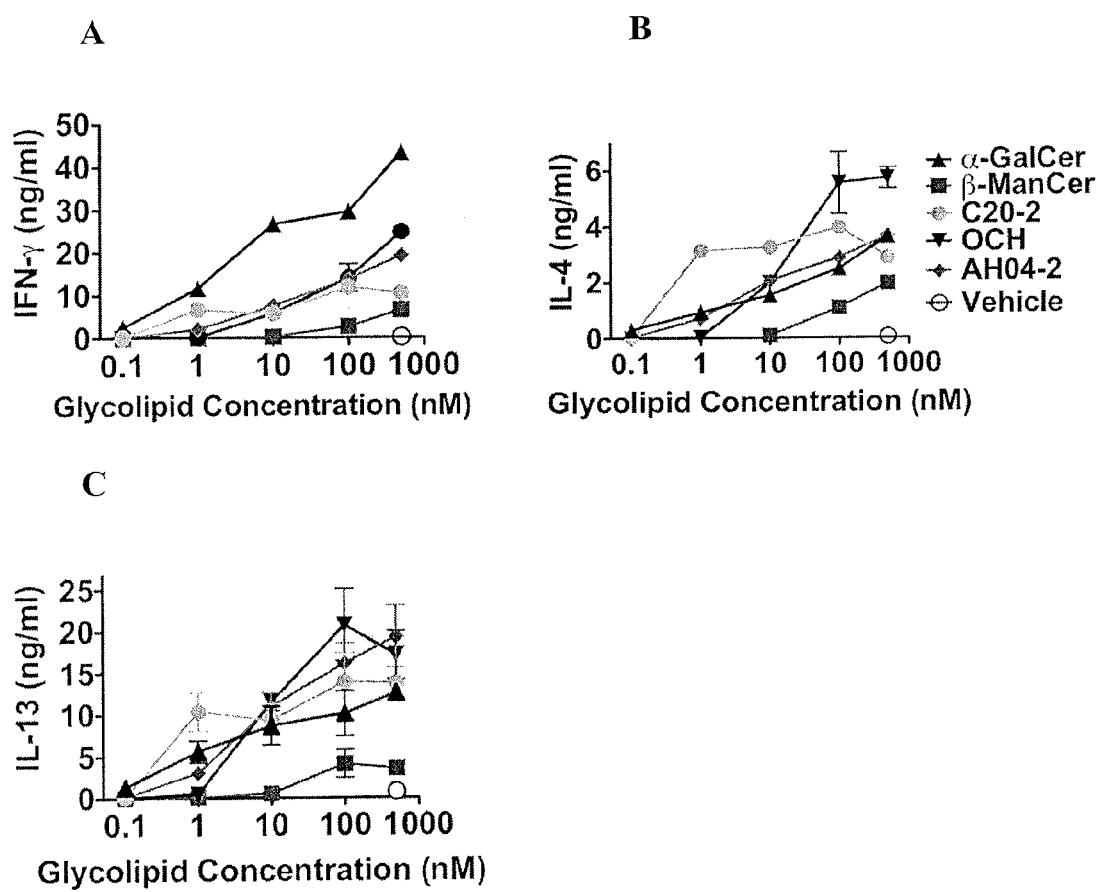

FIGS. 7A-7C shows in vitro cytokine production induced by glycolipid treatment. BALB/c splenocytes were stimulated with various concentrations of glycolipid or vehicle control for 48 hours, and the concentrations of IFN-γ (7A), IL-4 (7B), and IL-13 (7C) in supernatant were determined by ELISA. α-GalCer induced the greatest IFN-γ production, while C20:2, OCH, and AH04-2 induced a Th2-skewed cytokine profile with a lower IFN-γ level and higher amounts of IL-4 and IL-13.

FIGS. 8A-8E show graphs where the cytokine production induced by the glycolipid panel was tested in vivo. BALB/c mice were challenged with CT26 ($5 \times 10^5$) i.v. followed by 50 pmoles of glycolipid or vehicle control i.p. at time 0. Mice were bled retroorbitally at 0, 3, 6, 12, and 24 hours, and the amount of IFN-γ (8A), TNF-α (8B), IL-4 (8C), IL-12 (p70) (8D), and IL-13 (8E) in plasma was determined. Each data point represents mean±SD of triplicates. Due to significant overlap of data points corresponding to little or no detectable cytokine, some data points are not visible, but all compounds shown in legend were tested. α-GalCer induced the most IFN-γ in vivo, followed by C20:2, with C20:2 and α-GalCer induced similar levels of IL-12 and TNF-α. Little cytokine production was detected following OCH and AH04-2 administration. β-ManCer induced very little cytokine production except for some IL-12 and TNF-α.

Figure 9:
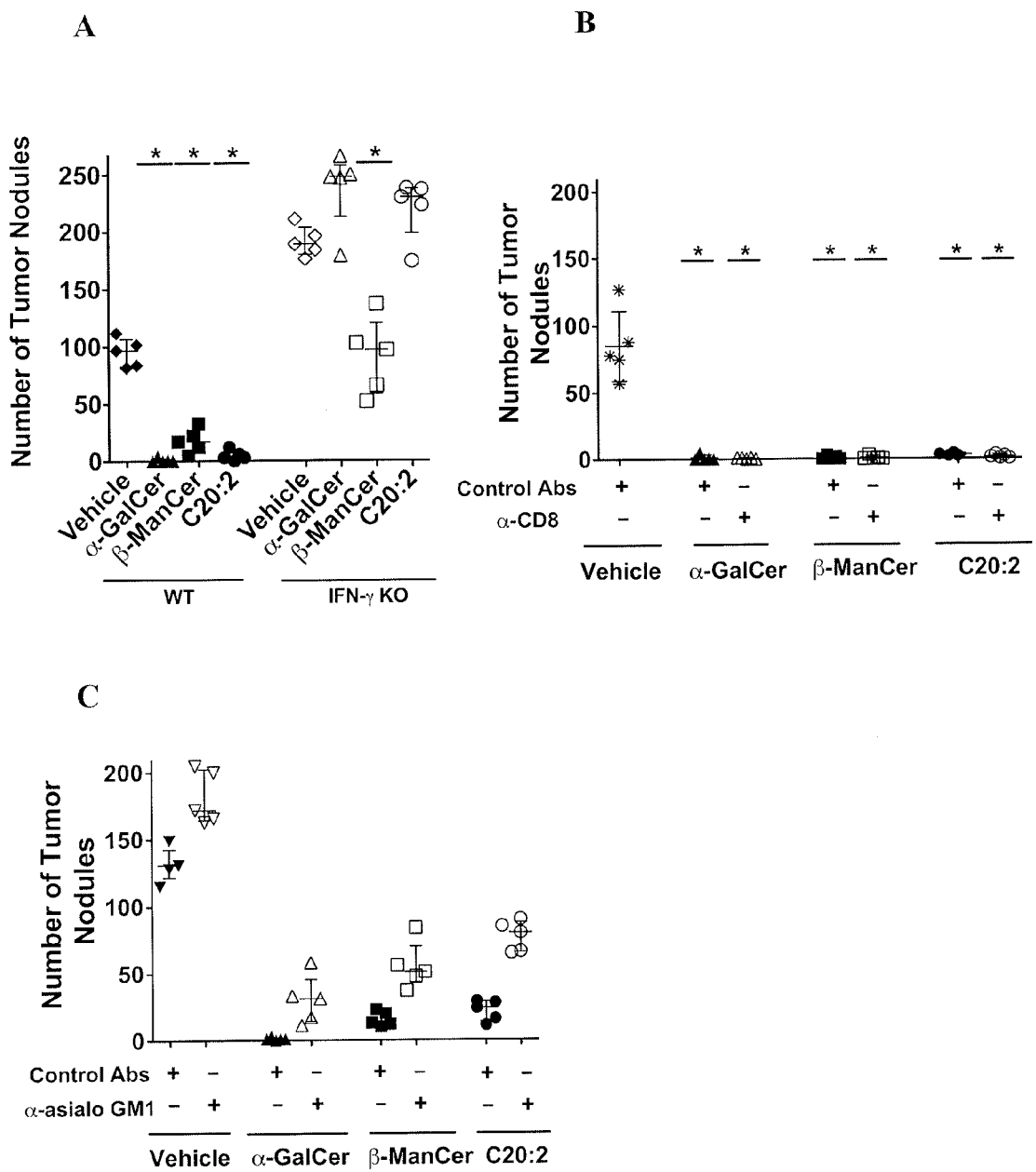

FIG. 9A is a graph illustrating that tumor protection induced by α-GalCer and C20:2, but not β-ManCer, is dependent on IFN-γ. CT26 cells ($5 \times 10^5$) were injected i.v. into the tail vein of BALB/c wild type or IFN-γ$^{-/-}$ mice on day 0 and glycolipids (50 pmoles) administered within one hour after tumor challenge. Mice were sacrificed 14-16 days after tumor challenge and lung metastases were enumerated. WT (closed symbols) or IFN-γ$^{-/-}$ (open symbols) were used. The data show that α-GalCer and C20:2 completely failed to induce any tumor protection in IFN-γ knockout mice, while β-ManCer treatment surprisingly still resulted in 50% fewer lung nodules compared to vehicle control mice (p=0.0079).

FIG. 9B is a graph showing that depletion of CD8+ cells had no effect on the number of lung nodules when compared to mice treated with control antibody. WT mice were treated with 200 μg anti-CD8 antibodies (open symbols) or rat IgG control antibodies (closed symbols) on days −1, 0, 5, and 10.

FIG. 9C is data showing that depletion of NKT cells with anti-asialo GM1 antibody resulted in a slight increase in tumor nodules, which was similar in all groups, including vehicle-treated mice. Mice were treated with 25 μl of anti-asialo GM1 antibodies (open symbols) or control rabbit serum (closed symbols) on days −1, 0, 5, and 10. (*, statistically significant from vehicle control, p<0.05)

FIG. 10A shows data from an experiment where mice were treated with L-NAME, which inhibits nitric oxide synthase (NOS) in vivo. Tumor protection induced by β-ManCer is NOS and TNF-α-dependent. CT26 cells ($5 \times 10^5$) were injected i.v. into the tail vein of BALB/c mice on day 0, and the glycolipids administered within one hour after tumor challenge. Mice were sacrificed 14-16 days after tumor challenge and lung metastases were enumerated. NOS inhibition had no effect on tumor formation in vehicle-, α-GalCer-, or C20:2-treated mice, as there was no difference between mice treated with L-NAME, or its inactive enantiomer, D-NAME.

FIG. 10B is a graph depicting WT and IFN-γ$^{-/-}$ mice treated with L-NAME (open symbols), or the inactive stereoisomer D-NAME (closed symbols), twice on days 0 and 1, and then once daily for days 2-14.

Figure 10:
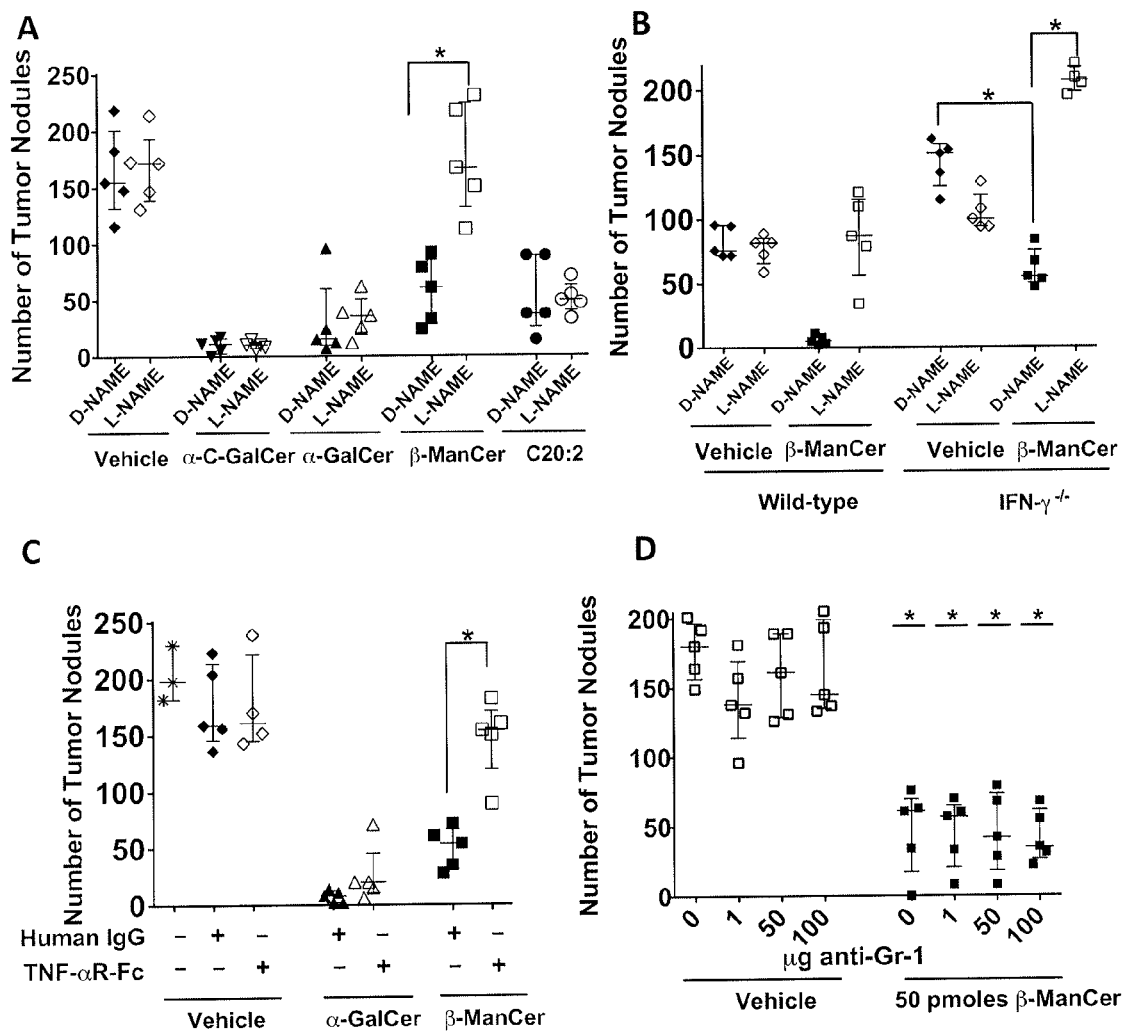

FIG. 10 C is graph depicting WT mice treated with etanercept (TNF-αR-Fc) (open symbols), or human IgG (closed symbols), every other day beginning the day of tumor challenge. Tumor protection by β-ManCer but not α-GalCer was TNF-α-dependent.

FIG. 10D is a graph showing WT mice were treated with the indicated concentration of anti-Gr-1 antibodies on days 1 and 2 after tumor challenge. (*, statistically significant from vehicle control or indicated group, p<0.05)

Figure 11:
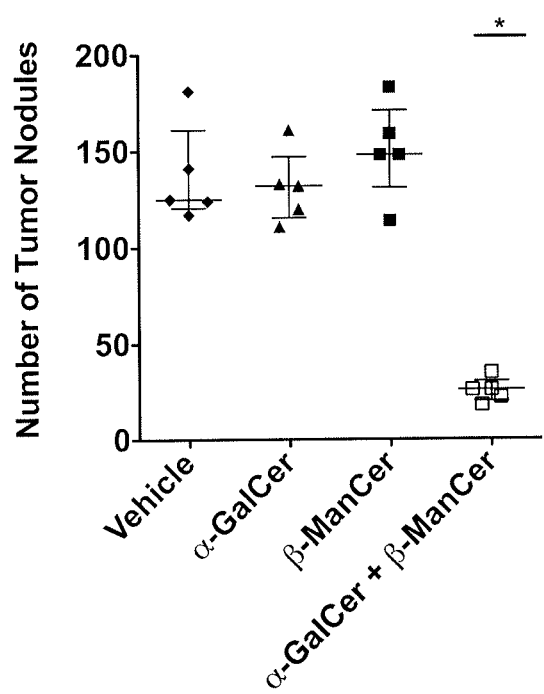

FIG. 11 is a graph depicting that simultaneous treatment with subtherapeutic doses of β-ManCer and α-GalCer induces synergistic tumor protection. CT26 cells ($5 \times 10^5$) were injected i.v. into the tail vein of BALB/c mice and vehicle (closed diamonds), 0.125 pmoles α-GalCer (filled triangles), 3 pmoles β-ManCer (filled squares), or 0.125 pmoles α-GalCer and 3 pmoles β-ManCer (open squares) was administered i.p. within one hour after tumor challenge.

Figure 12:
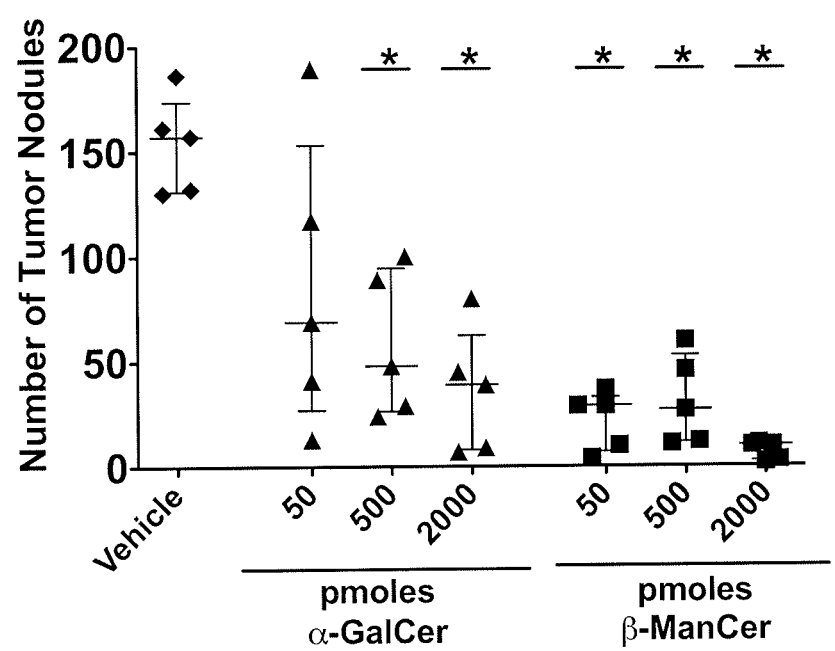

FIG. 12 shows that β-ManCer also protects against B16F10 melanoma metastases in C57BL/6 mice. B16F10 cells ($5 \times 10^5$) were injected i.v. into the tail vein of C57BL/6 mice. The indicated doses of glycolipid were administered within 1 hour. Mice were sacrificed 12-14 days after tumor challenge and lung metastases were enumerated. (*, statistically significant from vehicle control, p<0.05)

Figure 13:
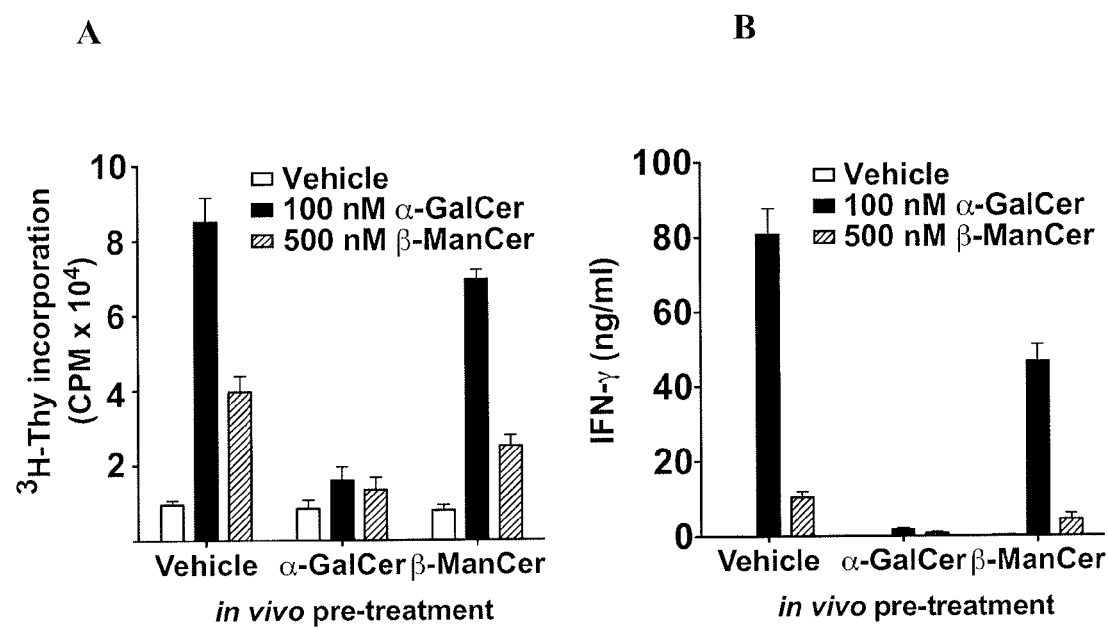

FIG. 13A is a graph showing splenocyte proliferation measured by $^3$H-thymidine incorporation during the final 8 hours of a 72-hour culture after being re-stimulated in culture. Pretreatment with α-GalCer induces anergy but pretreatment with (3-ManCer induces much less anergy.

FIG. 13B is a graph showing the amount of IFN-γ produced by the splenocyte culture after 48 hours of re-stimulation.

Figure 14:
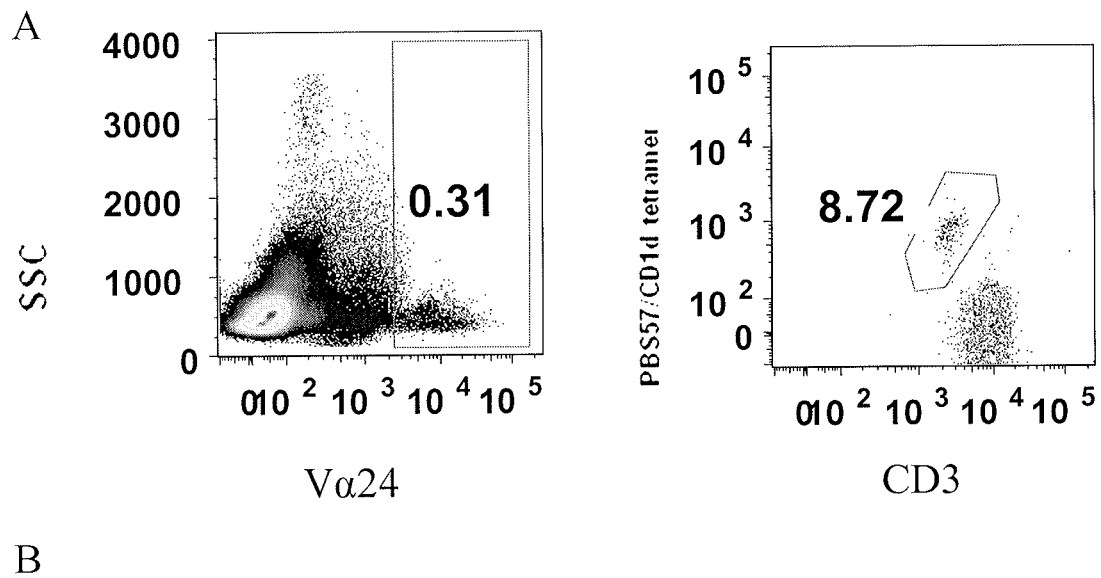
Figure 14:
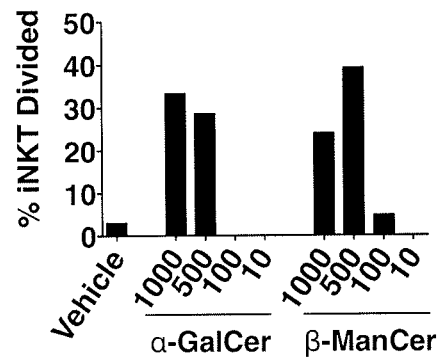
Figure 14:
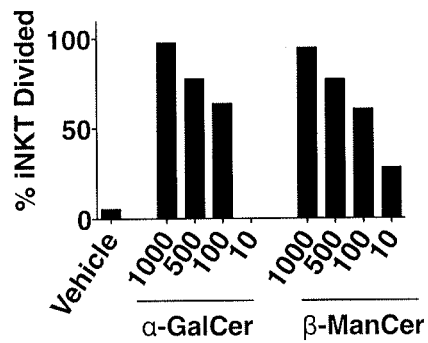

FIG. 14 shows the results of an experiment where human PBMCs were stimulated with β-ManCer or α-GalCer for 4 days. iNKT cells were defined as Vα24$_+$ CD3$^{Intermediate}$PBS57/CD1d tetramer$^+$ (FIG. 14A), and proliferation was measured by dilution of Cell-Trace Violet Dye. β-ManCer induced proliferation of human iNKT cells similar to that induced by α-GalCer (FIG. 14B).

DETAILED DESCRIPTION OF THE INVENTION

It was unexpectedly found that β-ManCer surprisingly induced protection against tumor formation in a iNKT cell-dependent manner, despite failure to induce substantial cytokine production. The induction of anti-tumor immunity by β-ManCer, or α-GalCer, occurred through distinct and synergistic mechanisms; the former dependent on nitric oxide and TNF-α, and the latter on IFN-γ.

In an embodiment, the present invention provides compositions for activating NKT cells in a mammal comprising a β-ManCer, or a salt or solvate thereof, in a pharmaceutically acceptable carrier.

In another embodiment, the present invention provides compositions for activating NKT cells in a mammal, the compositions comprising a β-ManCer or a salt or solvate thereof in a pharmaceutically acceptable carrier, wherein the β-ManCer comprises a sphingosine moiety and a fatty acid moiety comprising a linear or branched, saturated or unsaturated, aliphatic hydrocarbon group having from about 8 to about 49 carbon atoms. In another embodiment, the fatty acid moiety can comprise a linear or branched, saturated or unsaturated, aliphatic hydrocarbon group having from about 18 to about 49 carbon atoms. In a further embodiment, the fatty acid moiety can comprise a linear or branched, saturated or unsaturated, aliphatic hydrocarbon group having from about 8 to about 15 carbon atoms. In another embodiment, the fatty acid moiety can comprise a linear or branched, saturated or unsaturated, aliphatic hydrocarbon group having from about 18 to about 30 carbon atoms.

In yet another embodiment, the present invention provides compositions for activating NKT cells in a mammal, the compositions comprising a β-ManCer or a salt or solvate thereof in a pharmaceutically acceptable carrier, wherein the β-ManCer has the following structure:

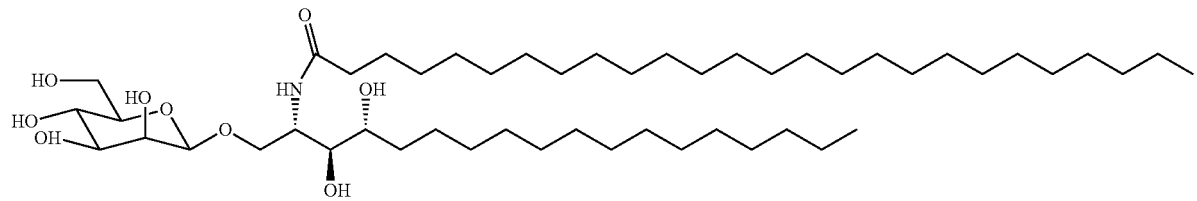 [SMILES: CCCCCCCCCCCCCCCCCCCCCCCCCC(=O)N[C@@H](COC1OC(CO)C(O)C(O)C1O)[C@H](O)[C@H](O)CCCCCCCCCCCCCC]

In yet another embodiment, the present invention provides a method for activating NKT cells in a subject comprising administering to the subject, a therapeutically effective amount of a pharmaceutical composition comprising β-ManCer, or a salt or solvate thereof, and a therapeutically effective amount of α-GalCer.

In a further embodiment, the present invention provides a method for activating NKT cells in a subject comprising administering to the subject, a therapeutically effective amount of a pharmaceutical composition comprising a therapeutically effective amount of: (i) β-ManCer, or a salt or a solvate thereof; (ii) GM-CSF; and (iii) other cytokines that induce cellular immunity such as IL-12 and/or IL-15.

In another embodiment, a method for activating NKT cells in a subject comprises administering to the subject, a therapeutically effective amount of pharmaceutical composition comprising β-ManCer, or a salt or solvate thereof, and a therapeutically effective amount of at least one or more T-cell co-stimulatory molecules or TLR ligands. The TLR ligands include, but are not limited to, ligands for TLR-2 (e.g., MALP-2), TLR3 (e.g., Poly I:C), TLR4 (e.g., LPS or monophosphoryl lipid A), TLR5 (e.g., flagellin), TLR7 (e.g., imiquimod), TLR8 (e.g., resiquimod), and TLR9 (e.g., CpG oligodeoxynucleotides). The co-stimulatory molecules, for example, can be selected from the group consisting of B7-1, B7-2, B7-3, B7-H, ICAM1, ICAM2, ICAM3, LFA1, LFA2, LFA3, CD40L, OX40L and 4-1BBL.

The compositions described herein can also include other immunostimulatory compounds. In an embodiment, the above compositions can also comprise a therapeutically effective amount of IL-2, and/or granulocyte/macrophage colony-stimulating factor (GM-CSF), and/or other cytokines that induce cellular immunity such as IL-12 and/or IL-15.

In a further embodiment, the present invention provides compositions for activating NKT cells in a subject comprising a β-ManCer or a salt or solvate thereof, and a therapeutically effective amount of an α-glycosylceramide, or a salt or solvate thereof. The α-glycosylceramide, in an embodiment, can be an α-galactosylceramide.

In a further embodiment, the present invention provides a composition comprising a therapeutically effective amount of a pharmaceutical composition comprising β-ManCer, or a salt or solvate thereof, and a therapeutically effective amount of at least one or more T-cell co-stimulatory molecules, or TLR ligands.

In a further embodiment, the present invention provides a composition comprising a therapeutically effective amount of a pharmaceutical composition comprising β-ManCer, or a salt or solvate thereof, and a therapeutically effective amount of at least one or more chemotherapeutic agents.

In an embodiment, the present invention provides a method for activating NKT cells in a subject comprising administering to the subject, a therapeutically effective amount of a pharmaceutical composition comprising β-ManCer, or a salt or solvate thereof.

In an embodiment, the present invention also provides methods for activating NKT cells in a subject. In particular, the present invention provides a method for activating NKT cells in a subject comprising administering to the subject, a therapeutically effective amount of a pharmaceutical composition comprising β-ManCer, or a salt or solvate thereof, and a therapeutically effective amount of IL-2.

The activated NKT cells are useful in treating or inhibiting the growth of tumors or neoplasms in a subject. In another embodiment, the present invention provides a method of treating or inhibiting the growth of tumor in a subject comprising administering to the subject a therapeutically effective amount of the pharmaceutical composition of β-ManCer, or a salt or solvate thereof, either as a monotherapy, or in conjunction with a therapeutically effective amount of an α-glycosylceramide, or a salt or solvate thereof, and/or at least one or more T-cell co-stimulatory molecules. The co-stimulatory molecules, for example, can be selected from the group consisting of B7-1, B7-2, B7-3, B7-H, ICAM1, ICAM2, ICAM3, LFA1, LFA2, LFA3, CD40L, OX40L and 4-1BBL.

In another embodiment, the present invention provides a method of treating or inhibiting cancer in a subject comprising administering to the subject a therapeutically effective amount of the pharmaceutical composition of β-ManCer or a salt or solvate thereof, either as a monotherapy, or in conjunction with a therapeutically effective amount of an α-glycosylceramide or a salt or solvate thereof, and/or at least one or more T-cell co-stimulatory molecules, or TLR ligands.

In an embodiment, the present invention provides a method for inducing an immune response in a subject comprising administering to the subject a therapeutically effective amount of the pharmaceutical composition of β-ManCer, or a salt or solvate thereof, either as a monotherapy, or in conjunction with a therapeutically effective amount of an α-glycosylceramide, or a salt or solvate thereof, and/or at least one or more T-cell co-stimulatory molecules or TLR ligands.

In an embodiment, the present invention provides a method for inducing an immune response in a subject comprising administering to the subject a therapeutically effective amount of the pharmaceutical composition of β-ManCer, or a salt or solvate thereof, with a vaccine. In accordance with the present invention the vaccine can be any vaccine, including for example, a vaccine such as a TARP 29-37-9V peptide, against prostate cancer, and Sargramostin (GM-CSF) emulsified in Montanide ISA 51 VG, to increase the vaccine efficacy.

In another embodiment, the present invention provides a method for inducing an immune response in a subject comprising contacting peripheral blood mononuclear cells of a subject in vitro, together with a vaccine, for example, such as a TARP 29-37-9V and an effective amount of the pharmaceutical composition of β-ManCer, or a salt or solvate thereof, and incubating the monocyte-derived dendritic cells made from patients' peripheral blood mononuclear cells together with the vaccine for a period of time, followed by administration of the cells into the subject. This combination would facilitate activation of the dendritic cells by NKT cells in the patients.

In accordance with the present invention, in an embodiment, the present invention provides a method for inducing an immune response in a subject comprising administering to the subject a therapeutically effective amount of the pharmaceutical composition of β-ManCer, or a salt or solvate thereof, in conjunction with one or more antibodies, including, for example, antibodies against CTLA-4 or PD-1 or TGF-beta. Blocking antibodies to these molecules can overcome negative regulation and enhance the effect of the β-ManCer.

In accordance with an embodiment, the present invention provides a pharmaceutical composition comprising β-ManCer or a salt or solvate thereof, wherein the β-ManCer comprises a sphingosine moiety and a fatty acid moiety comprising a linear or branched, saturated or unsaturated, aliphatic hydrocarbon group having from about 8 to about 49 carbon atoms, or the fatty acid moiety can comprise a linear or branched, saturated or unsaturated, aliphatic hydrocarbon group having from about 18 to about 49 carbon atoms, or the fatty acid moiety can comprise a linear or branched, saturated or unsaturated, aliphatic hydrocarbon group having from about 8 to about 15 carbon atoms, or the fatty acid moiety can comprise a linear or branched, saturated or unsaturated, aliphatic hydrocarbon group having from about 18 to about 30 carbon atoms, wherein the composition includes a pharmaceutically and physiologically acceptable carrier, in an amount effective for use in a medicament, and most preferably for use as a medicament for treating cancer, or inhibiting the growth of a tumor, or neoplasm in a subject, when administered to the subject in an effective amount.

In accordance with another embodiment, the present invention provides a pharmaceutical composition comprising β-ManCer or a salt or solvate thereof, having the following structure:

wherein the composition includes a pharmaceutically and physiologically acceptable carrier, in an amount effective for use in a medicament, and most preferably for use as a medicament for treating cancer, or inhibiting the growth of a tumor, or neoplasm in a subject, when administered to the subject in an effective amount.

In accordance with a further embodiment, the present invention provides a pharmaceutical composition comprising β-ManCer or a salt or solvate thereof, in an amount effective for use in a medicament, and most preferably for inducing an immune response in a subject, when administered to the subject in a therapeutically effective amount.

In an embodiment, the pharmaceutical compositions of the present invention for use in a medicament for treating cancer, or inhibiting the growth of a tumor, or neoplasm in a subject can comprise a therapeutically effective amount of: (i) β-ManCer, or a salt or a solvate thereof; and also include (ii) GM-CSF; and (iii) other cytokines that induce cellular immunity such as IL-12 and/or IL-15, and/or a therapeutically effective amount of α-GalCer and/or at least one or more T-cell co-stimulatory molecules or TLR ligands.

In another embodiment, the pharmaceutical compositions of the present invention are useful in a medicament for inhibiting the growth of a tumor selected from the group consisting of lung, breast, colon, liver, kidney, brain, neck, prostate, ovary, skin, and lymphoid tumors.

In a further embodiment, the pharmaceutical compositions of the present invention are useful in a medicament for treating cancers selected from the group consisting of melanoma, skin cancer, lung cancer, kidney cancer, stomach cancer, colon cancer, prostate cancer, breast cancer, ovarian cancer, and lymphoid cancer.

Additionally, NKT cells of a subject can be activated in vitro, and subsequently administered to the subject for use in the treatment or inhibition of the growth of a tumor, or cancer in the subject. In particular, in an embodiment, the present invention provides a method of treating or inhibiting the growth of a tumor or neoplasm in a subject comprising administering to the subject an effective amount of activated NKT cells derived from culturing in vitro a mononuclear cell fraction, the cell fraction comprising one or more NKT cells in the presence of β-ManCer, or a salt or solvate thereof, and optionally, an α-glycosylceramide, or a salt or solvate thereof. The method of treatment of a tumor can also encompass culturing in vitro, a mononuclear cell fraction, the cell fraction comprising a one or more NKT cells in the presence of β-ManCer, or a salt or solvate thereof, and optionally, an α-glycosylceramide, or a salt or solvate thereof, and at least one or more T-cell co-stimulatory molecules, or TLR ligands.

In another embodiment, the present invention provides a composition comprising the activated mammalian NKT cells, in an amount effective for use in a medicament, and most preferably for use as a medicament for treating cancer, or

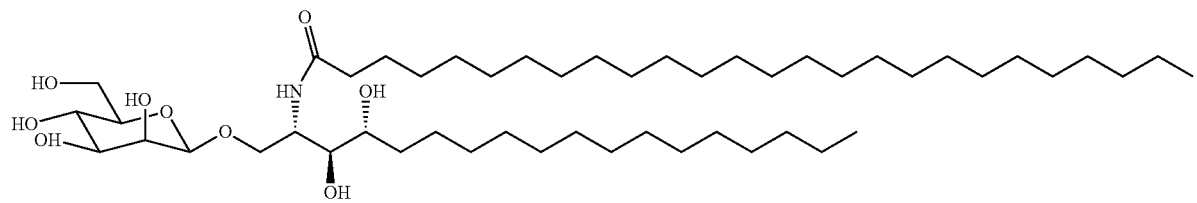 [SMILES: CCCCCCCCCCCCCCCCCCCCCCCCCC(=O)N[C@@H](COC1OC(CO)C(O)C(O)C1O)[C@H](O)[C@H](O)CCCCCCCCCCCCCC]

inhibiting the growth of a tumor, or neoplasm in a subject, when administered to the subject in a therapeutically effective amount.

In a further embodiment, it is contemplated that the composition comprising the activated mammalian NKT cells can be autologous, that is, derived from the subject being treated.

The term "naturally occurring" as used herein means an endogenous or exogenous protein isolated and purified from animal tissue or cells.

The term "isolated and purified" as used herein means a protein that is essentially free of association with other proteins or polypeptides, e.g., as a naturally occurring protein that has been separated from cellular and other contaminants by the use of antibodies or other methods or as a purification product of a recombinant host cell culture.

The term "biologically active" as used herein means an enzyme or protein or other molecule having structural, regulatory, or biochemical functions of a naturally occurring molecule.

The term "sphingosine" as used herein means 2-amino-4-octadecene-1,3-diol, which is an 18-carbon amino alcohol with a hydrocarbon chain that forms a primary portion of ceramide molecules.

The term "ceramide" as used herein, means one of a number of a class of sphingolipids, N-acyl derivatives with long chains of saturated or unsaturated fatty acids. The fatty acid moiety of ceramides can have carbon chain lengths from at least about eight carbons. In an embodiment, the fatty acid moiety of β-ManCer of the present invention can have anywhere from at least about eight carbons in length. For example, it can have a fatty acid moiety of between about 8 carbons to about 49 carbons in length, or for example, it can have a fatty acid moiety of between about 8 carbons to about 15 carbons in length. In another embodiment, the β-ManCer of the present invention can have a fatty acid moiety of between about 16 carbons and about 30 carbons in length.

In other embodiments the β-ManCer of the present invention can have a fatty acid moiety of between about 18 carbons and 49 carbons in length, for example, the fatty acid moiety can be about 18 carbons to about 30 carbons in length.

The therapeutic methods encompassed by the present invention involve treating primary tumors or cancers, as well as metastases. As an example, in one embodiment, a method for inhibiting or killing cancer cells comprises administering to a subject an effective amount of β-ManCer, or a salt or solvate thereof. As another example, in an embodiment, the activated NKT cells which were derived from culturing in vitro a mononuclear cell fraction, the cell fraction comprising a mammalian NKT cell in the presence of β-ManCer, or a salt or solvate thereof, and optionally, an α-glycosylceramide, or a salt or solvate thereof, or one or more cytokines, T-cell co-stimulatory molecules, TLR ligands, vaccines, or antibodies, to tumor or cancer cells in a subject.

In an embodiment of the present invention, the compositions and methods of treatment disclosed herein are useful against many mammalian tumors, including tumors arising from cancers of the lung, breast, colon, liver, kidney, brain, neck, prostate, ovary, skin, and lymphoid tumors. More specifically, the compositions and methods of treatment are useful in treating melanoma, skin cancer, lung cancer, kidney cancer, stomach cancer, colon cancer, prostate cancer, breast cancer, ovarian cancer, and lymphoid cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

The term "chemotherapeutic agents" as well as words stemming therefrom, as used herein, generally includes medications that work by interfering with DNA synthesis or function in cancer cells. Based on their chemical action at a cellular level, chemotherapy agents can be classified as cell-cycle specific agents (effective during certain phases of cell cycle) and cell-cycle nonspecific agents (effective during all phases of cell cycle). Without being limited to any particular example, examples of chemotherapy agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

In conjunction with the present invention, administration of β-ManCer can be used in combination with cancer vaccines as well as agents that block negative regulation of the immune system, such as anti-CTLA-4 monoclonal antibody, or anti-PD-1 antibody. It is also contemplated that β-ManCer can be used in conjunction with other cancer immunotherapies, such as Ontak (Denileukin diftitox, an IL-2-DPT fusion protein) and anti-CD20 (rituximab).

In another embodiment, administration of in vitro activated NKT cells of the present invention may also be accompanied by other treatments that are directed to tumor or cancer cells, for example, radiation, chemotherapy, and the like, as well as by adjunctive therapies to enhance the immune system's attack on the opsonized cancer or tumor cells, following the above-described treatment/therapy procedures.

In an embodiment, a growth factor, lymphokine, or cytokine is co-administered with β-ManCer, or a salt or solvate thereof. For example, GM-CSF (granulocyte/macrophage colony-stimulating factor), to stimulate the patient's white blood cells and support the immunocompetence status of the patient.

In an embodiment, β-ManCer, or a salt or solvate thereof, is delivered parenterally, such as by intravenous, subcutaneous, or intraperitoneal administration, e.g., injection. Suitable buffers, carriers, and other components known in the art can be used in formulating a composition comprising the β-ManCer, or a salt or solvate thereof, for suitable shelf-life and compatibility for the administration. These substances may include ancillary agents such as buffering agents and protein stabilizing agents (e.g., polysaccharides).

In one embodiment, the carrier is a pharmaceutically acceptable carrier. With respect to pharmaceutical compositions, the carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g. corn starch, pregelatinized starch), sugars (e.g., lactose, mannitol, sucrose, and dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include sodium chloride solution, Ringer's dextrose, dextrose and sodium chloride, lactated Ringer's and fixed oils. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compositions comprising β-ManCer may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

Therapeutic compositions are typically placed into a container having a sterile access port, for example, an intravenous solution bag or vial having a stopper pierceable by a hypodermic injection needle. The route of administration of β-ManCer, or a salt or solvate thereof, in accordance with the present invention, is in accord with known methods, e.g., injection or infusion by intravenous, intraperitoneal, intramuscular, intraarterial, subcutaneous, intralesional routes, by aerosol or intranasal routes, or by sustained release systems as noted below. β-ManCer, or its salts or solvates can be administered continuously by infusion or by bolus injection.

The choice of carrier will be determined, in part, by the chemical characteristics of β-ManCer, or a salt or solvate thereof, as well as by the particular method used to administer it. Accordingly, there are a variety of suitable formulations of the pharmaceutical composition of the invention. The following formulations for parenteral, subcutaneous, intravenous, intramuscular, intraarterial, intrathecal and interperitoneal administration are exemplary and are in no way limiting. More than one route can be used to administer β-ManCer, or a salt or solvate thereof, and in certain instances, a particular route can provide a more immediate and more effective response than another route.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of β-ManCer, or a salt or solvate thereof, administered should be sufficient to effect, e.g., a therapeutic or prophylactic response, in the subject over a reasonable time frame. The dose will be determined by the efficacy of β-ManCer, or a salt or solvate thereof, and the condition of a human, as well as the body weight of a human to be treated.

An effective amount of β-ManCer, or a salt or solvate thereof, to be employed therapeutically will depend, for example, upon the therapeutic and treatment objectives, the route of administration, the age, condition, and body mass of the patient undergoing treatment or therapy, and auxiliary or adjuvant therapies being provided to the patient. Accordingly, it will be necessary and routine for the practitioner to titer the dosage and modify the route of administration, as required, to obtain the optimal therapeutic effect. A typical daily dosage might range from about 0.1 μg/kg to up to about 100 μg/kg or more, preferably from about 0.1 to about 10 μg/kg/day depending on the above-mentioned factors. Typically, the clinician will administer the agent until a dosage is reached that achieves the desired effect. The progress of this therapy is easily monitored by conventional assays.

The dosage ranges for the administration of β-ManCer, or a salt or solvate thereof, are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication.

Generally, when β-ManCer, or a salt or solvate thereof, is administered together with additional therapeutic agents, lower dosages can be used. β-ManCer, or a salt or solvate thereof, can be administered parenterally by injection or by gradual perfusion over time. β-ManCer, or a salt or solvate thereof, can be administered intravenously, intraperitoneally, intramuscularly, subcutaneously, intracavity, or transdermally, alone or in combination with effector cells. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

The subject referred to in the inventive methods can be any subject. Preferably, the subject is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In accordance with the present invention, in an embodiment, β-ManCer may be administered to patients with a vaccine, including, for example, a vaccine such as a TARP 29-37-9V peptide, against prostate cancer, and Sargramostin (GM-CSF) emulsified in Montanide ISA 51 VG, to increase the vaccine efficacy. In another embodiment, β-ManCer can also be incubated with monocyte-derived dendritic cells made from patients' peripheral blood mononuclear cells together with a vaccine such as a TARP 29-37-9V peptide before administration of the cells into the patients. This combination facilitates the activation of the dendritic cells by NKT cells in the patients.

In accordance with the present invention, in an embodiment, β-ManCer may also be administered with antibodies, for example, including such as ones against CTLA-4 or PD-1 or TGF-beta. Blocking antibodies to these molecules can overcome negative regulation and enhance the effect of the β-ManCer.

EXAMPLES

The following examples further illustrate the invention but, of course, should not be construed as in any way limiting its scope.

Mice.

Female BALB/c and C57BL/6 mice were purchased from Animal Production Colonies, Frederick Cancer Research Facility, NCI. BALB/c Jα18$^{-/-}$ mice (provided by Masaru Taniguchi and Dale Umetsu) were bred at the National Cancer Institute under pathogen-free conditions. BALB/c IFNγ$^{-/-}$ mice were purchased from the Jackson Laboratory (Bar Harbor, Me.). Female mice older than 6 weeks of age were used for all experiments. All experimental protocols were approved by and performed under the guidelines of the National Cancer Institute's animal care and use committee.

Reagents.

Purified rat-anti mouse CD8 monoclonal antibody (clone 2.43) was obtained from Harlan Laboratories (Indianapolis, Ind.). Rabbit anti-asialo GM1 antibody was purchased from Wako Chemical Company (Richmond, Va.). Anti-mouse Gr-1 monoclonal antibody ascites (clone RB6-8C5) were purchased from Cedarlane Laboratories Ltd (Burlington, N.C.). Rat IgG control antibodies were purchased from Sigma-Aldrich, and control rabbit serum was obtained from Cedarlane Laboratories Ltd. N-nitro-L-arginine-methyl ester (L-NAME) and N-nitro-D-arginine-methyl ester (D-NAME) were purchased from Sigma-Aldrich (St. Louis, Mo.). TNF-αR-Fc (etanercept), a fusion protein of human TNF-α receptor with the Fc portion of human IgG1, was purchased from Amgen (Thousand Oaks, Calif.). Human IgG1 control antibodies were purchased from Invitrogen. The PPARγ inhibitor GW9662 was purchased from Cayman Chemical Company (Ann Arbor, Mich.).

Glycolipid synthesis.

α-GalCer (KRN7000) was purchased from Alexis Biochemicals (San Diego, Calif.). α-C-GalCer was obtained from the NIH Tetramer Core Facility at Emory University (Atlanta, Ga.).

The synthesis of β-mannosylceramide may be carried out using conventional methods including those described herein for exemplary Compound 1. In general, compound 1 may be obtained from the reaction between compound 2 and a desired electrophile (acid chloride) as shown below:

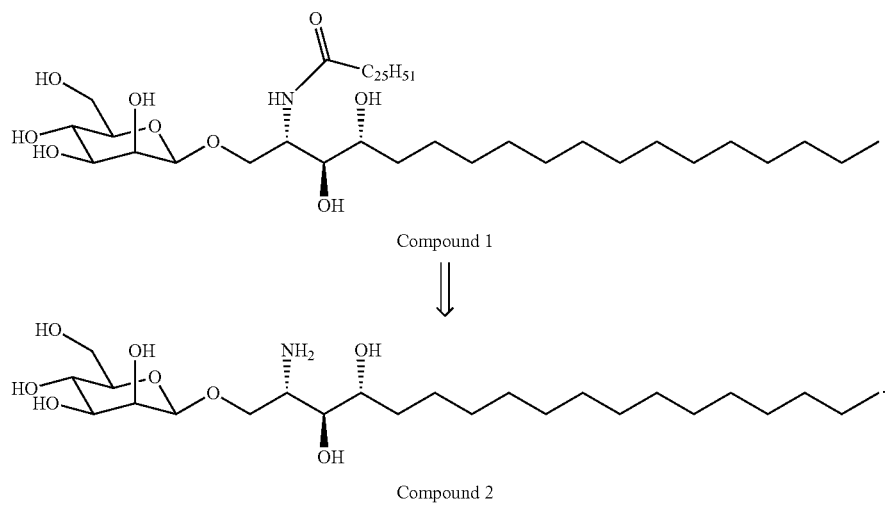

Compound 1

⇓

Compound 2

The synthesis of Compound 2 can be carried out as follows. The 1,2-O-stannylene acetal of D-mannose (Compound 3) was prepared using the procedure of Hodosi, G., et al., *J. Am. Chem. Soc.*, 119:2335-2336 (1997). Glycosyl bond formation with Compound 4 gave beta-mannoside (Compound 5). Compound 4,2-azido-3,4-isopropylidene-D-ribo-1-o-trifluoromethanesulfonyl 1,3,4-octadecanetriol was prepared from phytosphingosine (Avanti Polar Lipids, Alabaster, Al.). Following the procedure of van den Berg, R. J., et al., *Tetrahedron Letters* 43:8409-8412 (2002), the phytosphingosine was converted into an azide (Compound 6). The isopropylidene group was introduced by reaction with 2,2-dimethoxypropane giving (Compound 7). Compound 7 was converted to Compound 4 by reaction with trifluoromethanesulfonyl anhydride. Isopropylidene protection group from Compound 5 was removed using method reported by Dalpozzo, R., et al., *J. Org. Chem.*, 67:9093-9095 (2002), followed by reduction of the azide giving Compound 2. Reaction of Compound 2 with acid chlorides via Schmidt, R. R., et al., *Angew. Chem. Int. Ed. Engl.*, 25:725-726 (1986), can provide reasonable yields of betamannosylceramides. For example, Compound 1 was prepared from Compound 2 and hexacosanoyl chloride in 70%. The synthesized beta-mannosylceramides can be separated from a reaction mixture and further purified by a method such as column chromatography, high pressure liquid chromatography.

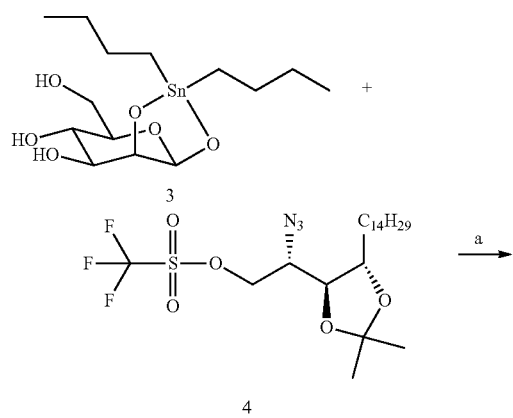

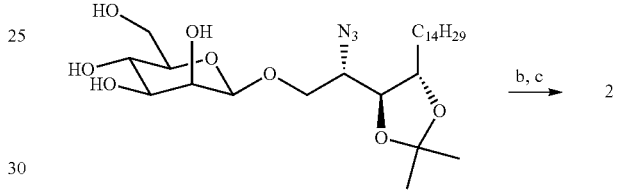

Reagents (yields in parentheses): a) CsF, DMSO, MS 4 Å, (60% yield); b) Ce(OTf)$_3$, CH$_2$Cl$_2$, CH$_3$NO$_2$ (quant.yield); c) H$_2$S, pyridine, H2O (80% yield).

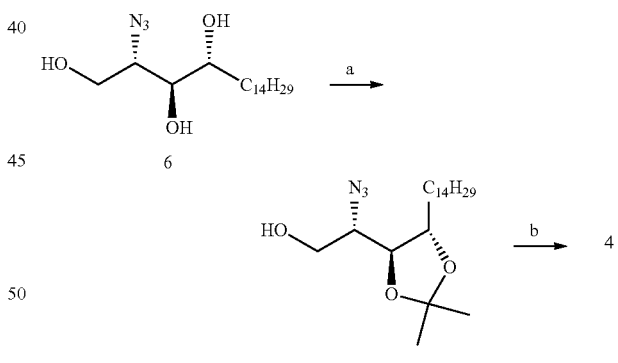

Reagents (yields in parentheses): a) 2,2-dimethoxypropane, TsOH (69% yield). b) Tf$_2$O, Et$_3$N, CH$_2$Cl$_2$ (quant. yield).

Preparation of 2-azido-3,4-isopropylidene-D-ribo-1, 3,4-octadecanetriol (Compound 7)

Compound 6 (1.0 g, 2.91 mmol) and 2,2-dimethoxypropane (40 ml) were treated with toluene-p sulfonic acid (20 mg) for 14 hours at room temperature. The mixture was then neutralized with saturated aqueous sodium hydrogen carbonate (10 ml) and the product was extracted with EtOAc (3×20 ml). The combined extracts were washed with water (2×20 ml), dried over Na$_2$SO$_4$ and concentrated under reduced pressure. The desired product (Compound 7) (770 mg, 69% yield) was obtained as a clear oil after chromatography (SiO$_2$, hexane:EtOAc 5:1). NMR (1H, CDCl$_3$) δ 4.21 (m, 1H), 4.05-3.88 (m, 2H), 3.90 (dd, J=11.0, 4.2 Hz, 1H), 3.44 (m, 1H), 2.09 (bs, 1H, HO-1), 1.52 (m, 2H), 1.48 (s, 3H), 1.22 (s, 3H), 1.26-1.19 (m, 24H), 0.85 (t, J=6.2 Hz, 3H); NMR (13C, CDCl$_3$) δ 107.4, 77.0, 75.4, 62.9, 60.2, 30.9, 28.7, 28.6, 28.4, 28.3, 27.0, 25.5, 24.6, 21.7, 12.1. ES-MS m/e ([M+Na]$_+$) 406.2

Preparation of 2-azido-3,4-isopropylidene-D-ribo-1-O-trifluoromethanesulfonyl-1,3,4-octadecanetriol (Compound 4)

Et$_3$N (0.243 ml, 2.0 mmol) and triflic anhydride (0.323 ml, 1.92 mmol) were added to a solution of lipid (Compound 7) (700 mg, 1.82 mmol) in CH$_2$Cl$_2$ (8 ml) at −20° C. The reaction mixture was stirred for 1 hour and saturated aqueous sodium hydrogencarbonate (1 ml) was added. The product was extracted with CH$_2$Cl$_2$(3×10 ml), and the combined extracts were dried over Na$_2$SO$_4$ and concentrated under reduced pressure. The crude compound 4 was employed in the next step without further purification. NMR (1H, CDCl$_3$) δ 4.84 (dd, J=11.0, 2.4 Hz, 1H), 4.76 (dd, J=11.0, 4.2 Hz, 1H), 4.21 (m, 1H), 4.05 (m, 1H), 3.74 (m, 1H), 1.52 (m, 2H), 1.48 (s, 3H), 1.22 (s, 3H), 1.26-1.19 (m, 24H), 0.85 (t, J=7.0 Hz, 3H).

Preparation of 2-azido-3,4-isopropylidene-D-ribo-1-O-β-mannopyranosyl-1,3,4-octadecanetriol (Compound 5)

Mannose donor (Compound 3) (3.0 g, 7.3 mmol) was dissolved in anhydrous DMSO (12 ml), molecular sieves (4 Å, 1 g) and CsF (1.09 g, 7.2 mmol) was added. After addition of lipid (Compound 4) (930 mg, 1.82 mmol), the mixture was stirred vigorously at 24° C. for 36 hours, and concentrated. The residue was triturated with acetonitrile (20 ml), the resulting suspension was filtered through a pad of Celite, solids were washed with acetonitrile (3×10 ml), and the combined filtrate was concentrated. The residue was purified chromatographically (SiO$_2$, CH$_2$Cl$_2$:MeOH, 14:1) to give Compound 5 (580 mg, 60% yield) as a solid foam. NMR (1H, CD$_3$OD:CDCl$_3$ 3:1) δ 4.59 (bs, 1H), 4.15 (m, 1H), 4.08 (dd, J=11.0, 7.4 Hz, 1H), 4.00 (J=11.0, 2.5 Hz, 1H), 3.95 (dd, J=9.6, 5.2 Hz, 1H), 3.91 (dd, J=2.9 Hz, 1H), 3.87 (dd, J=11.6, 2.4 Hz, 1H), 3.74 (dd, J=11.8, 5.4 Hz, 1H), 3.63-3.58 (m, 2H), 3.45 (dd, J=9.4, 2.9 Hz, 1H), 3.22 (m, 1H), 1.66-1.51 (m, 4H), 1.38 (s, 3H), 1.29 (s, 3H), 1.29-1.25 (m, 22H), 0.87 (t, J=6.9 Hz, 3H). NMR (13C, CD$_3$OD:CDCl$_3$ 3:1) δ 109.3, 101.2 (Jc1, H=157 Hz, C1 mannose), 78.4, 76.6, 74.9, 72.4, 71.2, 70.8, 68.1, 62.5, 60.6, 32.9, 30.2, 28.4, 27.8 24.6, 15.0. ES-MS m/e ([M+Na]+) 568.4

Preparation of 2-amino-1-O-β-mannopyranosyl-D-ribo-1,3,4-octadecanetriol (Compound 2)

To a solution of (Compound 5) (500 mg, 0.92 mmol) in wet nitromethane (2 ml) and CH$_2$Cl$_2$ (1 ml) was added Ce(OTf)$_3$ (83 mg, 0.3 mmol) with vigorous stirring. The reaction mixture was stirred at 40° C. for 2 hours and saturated aqueous sodium hydrogencarbonate (3 ml) was added. The product was extracted with CH$_2$Cl$_2$ (3×8 ml), and the combined extracts were dried over Na$_2$SO$_4$ and concentrated under reduced pressure. The crude compound was employed in the next step without further purification. ES-MS m/e ([M+Na]+) 528.2.

A solution of compound in pyridine-water (5:1, 3 ml) was saturated with H$_2$S and stirred for 24 hours at 24° C. under H$_2$S. The solution was concentrated under reduced pressure. Reaction mixture was dissolved in CHCl$_3$-MeOH (6:1) and passed through silica pad (CHCl$_3$-MeOH 6:1, as eluent). The solvents were concentrated under reduced pressure to give Compound 2 as a white solid (350 mg, 0.73 mmol, 80% yield). NMR (1H, CD$_3$OD:CDCl$_3$ 2:1) δ 4.50 (bs, 1H), 4.05 (dd, J=11.0, 3.8 Hz, 1H), 3.86 (dd, J=11.0, 2.5 Hz, 2H), 3.69 (m, 2H), 3.62-3.44 (m, 4H), 3.41 (dd, J=9.4, 2.9 Hz, 1H), 3.19 (m, 1H), 1.64-1.55 (m, 2H), 1.29-1.25 (m, 24H), 0.92 (t, J=6.9 Hz, 3H). ES-MS m/e ([M+H]+) 480.3, ([M+Na]+) 502.3.

Preparation of 2-hexacosanoylamino-1-O-β-mannopyranosyl-D-ribo-1,3,4-octadecanetriol (Compound 1)

To a solution of lipid (Compound 2) (100 mg, 0.21 mmol) in tetrahydrofuran-50% NaOAc in water (2:1.5) was added hexacosanoyl chloride (130 mg, 0.32 mmol) with vigorous stirring. The reaction mixture was stirred at 24° C. for 4 hours. The organic phase was separated and the water phase was extracted with tetrahydrofuran (3×4 ml), and the combined extracts and organic phase were dried over Na$_2$SO$_4$ and concentrated under reduced pressure. The residue was purified chromatographically (SiO$_2$, CH$_2$Cl$_2$:MeOH, 11:1) to give Compound 1 (127 mg, 70% yield) as a white solid. NMR (1H, CD$_3$OD:CDCl$_3$ 1:2) δ 4.50 (bs, 1H), 4.16 (m, 1H), 4.05 (dd, J=11.0, 3.8 Hz, 1H), 3.86 (dd, J=11.0, 2.5 Hz, 2H), 3.69 (m, 2H), 3.62-3.44 (m, 3H), 3.41 (dd, J=9.4, 2.9 Hz, 1H), 3.19 (m, 1H), 2.19 (t, J=6.7 Hz, 2H), 1.61 (m, 4H), 1.29-1.25 (m, 68H), 0.92 (t, J=6.9 Hz, 6H). High resolution ES-MS m/e ([M+Na]+) 880.7218.

The compounds C20:2, OCH, and AH04-2 were synthesized and solubilized for in vitro, or in vivo use, as previously described in Yu, K. O., et al., *Proc Natl. Acad. Sci. USA*, 102:3383-3388 (2005); Ndonye, R. M., et al., *J. Org. Chem.*, 70:10260-10270 (2005); and Forestier, C., et al., *J. Immunol.*, 178:1415-1425 (2007).

Cell Lines.

The CT26 colon carcinoma and B16F10 melanoma cell lines were maintained in RPMI 1640 and DMEM medium, respectively, supplemented with 10% FCS, L-glutamine, sodium pyruvate, nonessential amino acids, and 2-mercaptoethanol (5×10$^{-5}$M). Cells were cultured in an atmosphere of 37° C. and 5% CO$_2$. iNKT hybridoma cell lines 24.9.E and DN32.D3 were obtained from Samuel Behar (Harvard Medical School) and Albert Bendelac (University of Chicago, Chicago, Ill., USA) and were cultured in RPMI 1640 medium containing the supplements listed above. Cells were cultured in an atmosphere of 37° C. and 5% CO$_2$.

In Vivo Lung Metastasis Assay.

5×10$^5$ CT26 cells in 0.2 ml PBS were injected i.v. into the tail vein. Glycolipid or vehicle control (0.00025% Tween 20) was injected i.p. (in 0.2 ml PBS) within one hour after tumor challenge. Mice were sacrificed 12-16 days after tumor challenge, and lungs were stained and fixed and metastases were enumerated as previously described (Park, J. M., et al., *International J. of Cancer*, 114:80-87 (2004)). The same protocol was used for the B16F10 cell line, except that lungs were perfused with PBS instead of ink before removal.

For CD8$^+$ T and NK cell depletion, mice were treated with anti-CD8 (200 μg/injection), anti-asialo GM1 (25 μl/injection), or control antibodies 1 day prior to tumor challenge, the day of challenge, and 5 and 10 days following tumor challenge. CD8$^+$ T and NK cell depletion of >90% was confirmed by flow cytometric staining for CD8 (clone 53-6.7, BD Biosciences, Rockville, Md.) and pan-NK cell marker (clone DX5, eBioscience, San Diego, Calif.) at the conclusion of the experiment. For Gr-1+ cell depletion, mice were injected i.p. with 100, 50, or 1 μg anti-Gr-1 antibody, 16 and 40 hours after tumor challenge. CD11b+Gr-1$^{high}$ cell depletion of >99% and CD11b+Gr-1$^{intermediate}$ cell depletion of >80% by 100 μg of anti-Gr-1 antibodies, was confirmed by flow cytometric staining for CD11b (clone M1/70, eBioscience), Gr-1 (clone RB6-8C5, BD Biosciences), Ly-6C (clone AL-21, BD Biosciences) and Ly6G. (clone 1A8, BD Biosciences). Where indicated, mice received 0.2 mg L-NAME or D-NAME i.p. twice per day on the day of tumor challenge, the day after tumor challenge, and once daily for 2 weeks after tumor injection. Blockade of TNF-α was achieved by administration of 100 μg of etanercept every other day, beginning immediately following tumor challenge, per the method of Fichtner-Feigl, S., et al., *Cancer Res.*, 68:3467-3475 (2008). For PPARγ inhibition, mice were treated 0.15 mg/ml GW9662 (200 μL i.p.) or vehicle control (0.5% DMSO in PBS) immediately following tumor challenge, and then 30 minutes prior to glycolipid administration, via the method of Coste, A., et al., *J. Immunol.*, 180:4939-4947 (2008).

In Vitro iNKT Activation.

Splenocytes were harvested from mice (n=3), and erythrocytes were depleted with ACK Lysis Buffer (Lonza, Walkersville, Md.). Cells were labeled with 0.1 μM CFSE (Invitrogen, Carlsbad, Calif.) for 15 minutes at room temperature. Labeled cells (4 10$^6$ cells/well of 24-well plate) were stimulated for 3.5 days with glycolipid or vehicle control. At the end of the culture, cells were harvested and stained with PBS57-loaded CD1d tetramer (NIH Tetramer Facility) and anti-CD3 (clone 145-2C11, Biolegend). The fluorescence of stained cells was measured by FACSCalibur (BD Biosciences), and data were analyzed by Flowjo (Tree Star, Inc., Ashland, Oreg.).

In Vitro TNF-α Production by iNKT Cells.

Splenocytes were harvested from mice (n=3), and erythrocytes were depleted with ACK Lysis Buffer (Lonza). Cells (4 10$^6$ cells/well of 24-well plate) were stimulated overnight with 100 nM β-ManCer or vehicle control. At the end of the culture, cells were harvested and stained with PBS57-loaded CD1d tetramer (NIH Tetramer Facility) and anti-CD3 (clone 145-2C11, Biolegend, San Diego, Calif.). Cells were fixed and permeabilized with the Cytofix/Cytoperm Fixation/Permeabilization Solution Kit (BD Biosciences) and stained for intracellular TNF-α (clone MP6-XT22, BD Biosciences). The fluorescence of stained cells was measured by FACSCalibur (BD Biosciences), and data were analyzed by Flowjo (Tree Star).

Plate-Bound mCD1d Hybridoma Stimulation Assay.

Protocol was modified from that of Gumperz et al. (Gumperz, J. E., et al., *Immunity*, 12(2):211-221 (2000)). mCD1d dimer/Ig fusion protein (BD Biosciences) was incubated with the indicated concentrations of glycolipid in pH 5 sodium acetate buffer containing 0.01% Tween20 and 45 μg/ml saposin C (provided by Nico Tjandra and Motoshi Suzuki [both from National Heart, Lung, and Blood Institute, NIH, Bethesda, Md., USA]) overnight at 37° C. The mCD1d dimers loaded with glycolipid were loaded onto 96-well Protein G Plates (Pierce, Rockford, Ill.) and incubated for 48 hours at 37° C. The plates were washed with PBS and tissue culture media to remove anything not coated on the plates. 1 10$^5$ 24.9.E or DN32.D3 iNKT hybridoma cells were added to each well and incubated at 37° C. and 5% CO$_2$ for 24 hours. Supernatants were collected and analyzed for IL-2 by ELISA.

Visualizing Liver iNKT Cells with Glycolipid-Loaded CD Dimers.

mCD1d/Ig fusion protein (CD1d dimers; BD Biosciences) was loaded with glycolipid at 37° C. overnight. PE-anti-mouse IgG antibodies were added and incubated for 1 hour at room temperature, and mouse IgG isotype control was added for an additional 30 minutes at room temperature to saturate unbound excess anti-IgG antibodies. Livers were perfused with Liver Perfusion Medium (Invitrogen), and a single cell suspension was prepared in Liver Digest Medium (Invitrogen) and incubated at 37° C. for 20 minutes. Hepatocytes were removed from the suspension by centrifugation (30 g for 1 minute), and liver lymphocytes were then purified from the cell suspension by a 40%/80% gradient of Percoll (Sigma-Aldrich). Liver lymphocytes were stained with CD dimers for 1 hour at 4° C., followed by staining with anti-CD3 (clone 145-2C11, Biolegend). The fluorescence of stained cells was measured by FACSCalibur (BD Biosciences), and data were analyzed by Flowjo (Tree Star).

In Vitro Cytokine Assay.

Splenocytes (8×10$^5$/well of 96 well plates) from BALB/c mice were stimulated with glycolipid or solvent control for 48 hours. Supernatants were collected, and the concentration of IFN-γ, IL-4, or IL-13 was determined by ELISA.

In Vivo Cytokine Assay.

The concentration of IFN-γ, IL-4, IL-13, IL-12 (p70), and TNF-α in plasma samples was determined by MILLIPLEX cytokine multiplex immunoassay kit (Millipore, Billerica, Mass.) using a Bio-Plex system (Bio-Rad, Hercules, Calif.) according to manufacturer's instructions.

Human iNKT Cell Activation.

Human PBMCs from anonymous blood bank buffy coats (obtained with NIH approval) were separated by density centrifugation over a Ficoll-Paque gradient (GE Healthcare). Cells were labeled with 1 μM CellTrace Violet Cell Proliferation Dye (Invitrogen) for 15 minutes at room temperature. Labeled cells (4 10$^6$ cells/well of 24 well plate) were stimulated for 4 days with glycolipid or vehicle control. At the end of the culture, cells were harvested and stained with PBS57-loaded CD1d tetramer-APC (NIH Tetramer Facility), anti-Vα24-PE (clone C15, Beckman Coulter), anti-CD3-PE-Cy7 (clone UCHT1, BioLegend), and yellow LIVE/DEAD Fixable Dead Cell Stain (Invitrogen). The fluorescence of stained cells was measured by LSRII (BD Biosciences), and data were analyzed by FlowJo (Tree Star). iNKT cells were identified by gating on lymphocytes and live cells, followed by Vα24+CD3$^{intermediate}$PBS57/CD1d tetramer+ cells. The percentage of iNKT cells that divided was determined by the percentage that had diluted the proliferation dye.

Statistical Analysis.

The data were analyzed using the nonparametric Mann-Whitney test by using GraphPad Prism software (version 5; GraphPad software, La Jolla, Calif.). The data were considered significant at p<0.05. All experiments were repeated at least twice to confirm reproducibility of results.

Example 1

This example demonstrates how β-ManCer specifically induces strong protection against CT26 lung metastasis in an iNKT cell-dependent manner.

Figure 1:
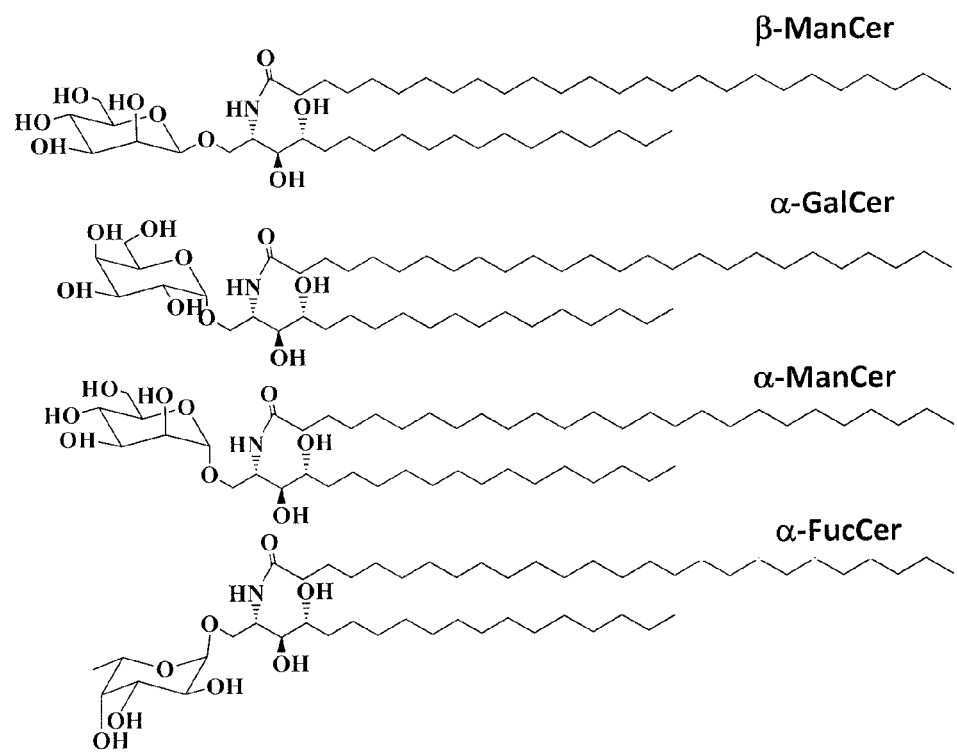

The anti-tumor activity of a panel of synthetic glycosylceramides (FIG. 1) in a lung metastasis model of the CT26 colon carcinoma was examined. This panel included β-ManCer, containing the same ceramide tails as the prototypical iNKT cell antigen, α-GalCer, as well as α-ManCer, and α-FucCer. The activity of these compounds was compared to that of α-GalCer. Surprisingly, strong protection induced by β-ManCer at a low dose of 50 pmoles (FIG. 2A), which was similar to protection following treatment with α-GalCer. α-FucCer and α-ManCer failed to induce any tumor protection except at a high dose (5000 pmoles) of α-ManCer (FIG. 2A). β-ManCer was 100-fold more potent than α-ManCer and fβ-GalCer, as 5,000 pmoles of α-ManCer or β-GalCer induced protection comparable to that induced by 50 pmoles of β-ManCer.

Figure 2:
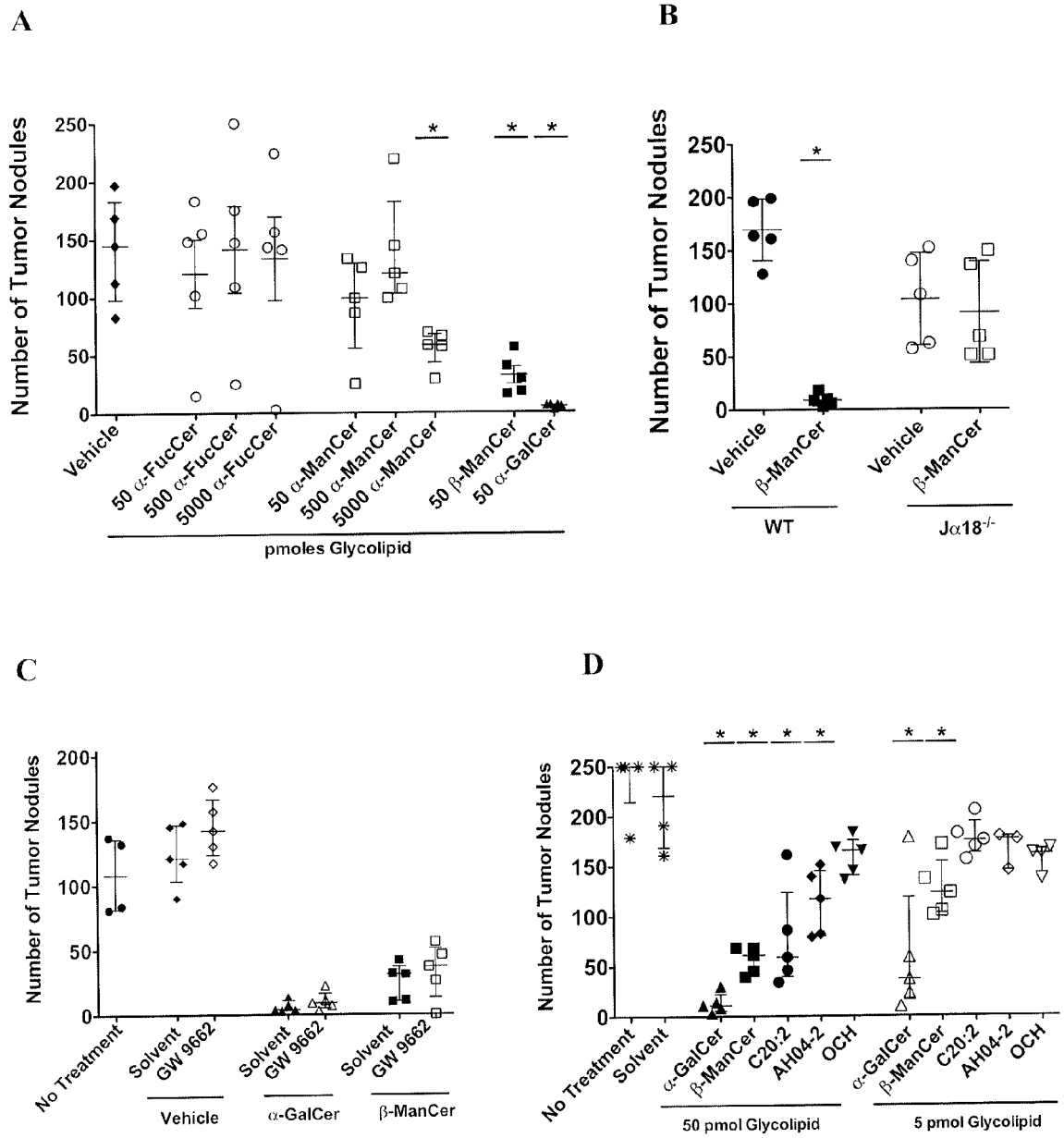

To rule out the possibility that β-ManCer was inducing tumor protection by a mechanism independent of iNKT cells, the ability of β-ManCer to protect in Jα18KO mice, which lack only iNKT cells was tested. All protection was lost in Jα18KO mice, confirming that β-ManCer is also iNKT-specific (FIG. 2B). Inhibition of peroxisome proliferator-activated receptor-γ (PPARγ), a transcription factor that regulates mannose receptor expression, with the irreversible inhibitor GW 9662 had no effect on β-ManCer-induced protection (FIG. 2C), supporting the findings that protection induced by β-ManCer is completely dependent on type I NKT cells, and is not due to signaling through the mannose receptor.

The activity and mechanism of action of β-ManCer were then compared to those of α-GalCer, as well as two previously described α-GalCer analogs, C20:2 and OCH, both known to activate iNKT cells, but induce cytokine profiles more skewed towards a Th2 response. Also included in this study was AH04-2, the aminodiol analog of OCH, which has been shown to have a similar cytokine profile to OCH. A rank order of tumor protection was established at a dose of 50 pmoles (FIG. 2D), although all glycolipids tested elicited protection at doses≥500 pmoles (data not shown). α-GalCer induced the greatest protection, followed by β-ManCer and C20:2, which were similarly protective. In contrast, AH04-2 and OCH induced significantly less tumor killing. The 50 pmole dose was utilized in subsequent in vivo experiments to investigate correlates of tumor protection. The results at the 5 pmole dose indicate that α-GalCer is still about a log more potent than β-ManCer.

Example 2

This example characterizes the ability of β-ManCer to activate iNKT cells.

Figure 3:
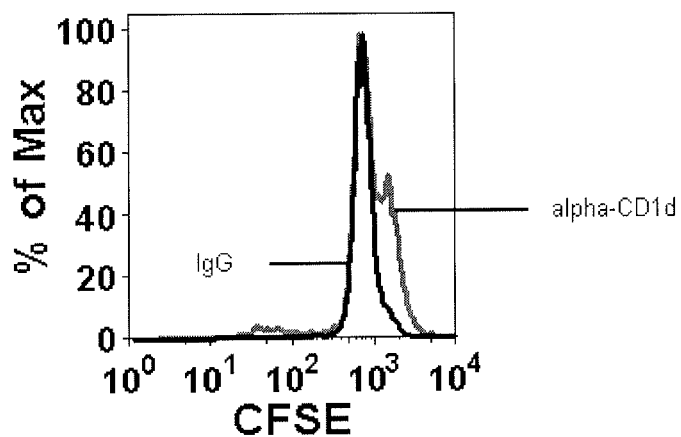
Figure 3:
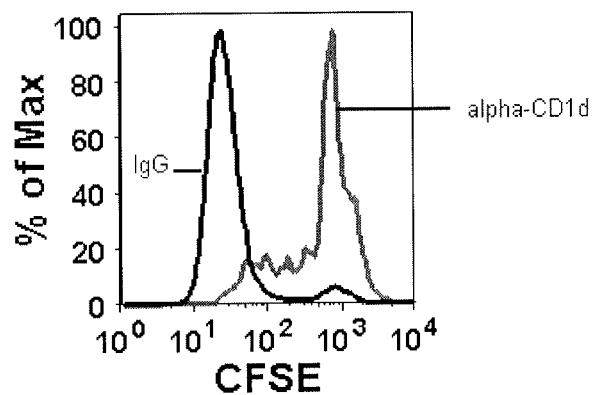
Figure 3:
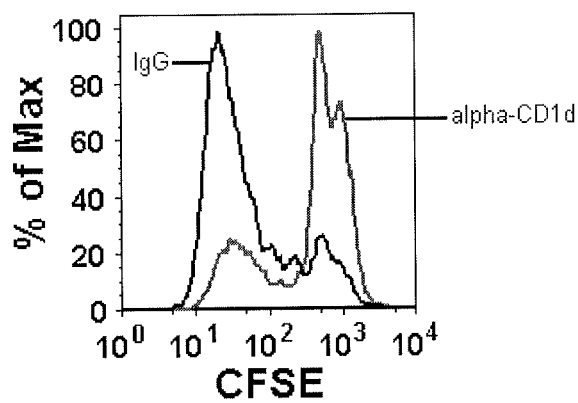

Mouse splenocytes were stimulated overnight with α-GalCer or β-ManCer, and iNKT cell activation was measured by upregulation of activation markers CD25 and CD69. iNKT cells express low levels of CD69, and this expression increases upon activation. β-ManCer induced upregulation of CD25 and CD69 on iNKT cells, albeit not to the same extent as that after α-GalCer stimulation (data not shown). β-ManCer also induced proliferation of 40% of iNKT cells, as measured by CFSE dilution after a 3.5-day stimulation, comparable to α-GalCer, which induced proliferation of 44% of iNKT cells, and this proliferation was inhibited to 5.4% (86% inhibition) with a CD1d-blocking antibody, confirming that iNKT cells recognize β-ManCer in the context of CD1d (FIG. 3).

Figure 4:
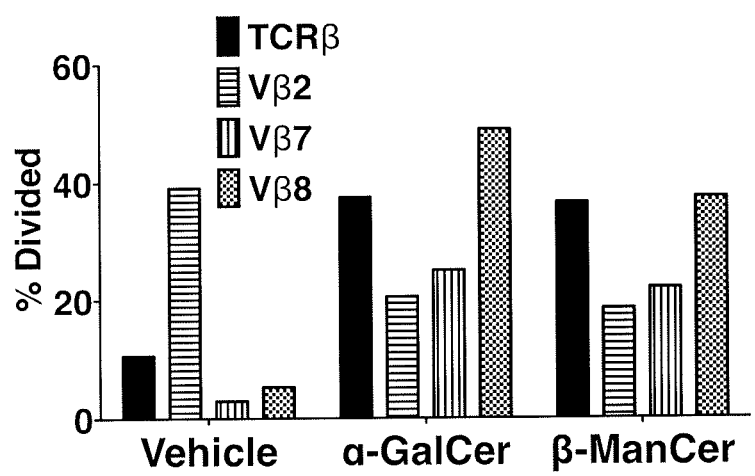
FIG. 4 is a bar graph showing the proliferation of different Vβ+ iNKT cell subsets by CFSE dilution characterized after a 3.5-day stimulation. β-ManCer and α-GalCer induced similar proliferation of the different Vβ subsets of iNKT cells.

Additionally, experiments were undertaken to determine whether β-ManCer stimulated only a subset of iNKT cells. While iNKT cells use the semi-invariant TCRα chain, this can pair with multiple Vβ chains (Vβ2, Vβ7, and Vβ8 in mice). We characterized the proliferation of different Vβ$^+$ iNKT cell subsets by CFSE dilution after a 3.5-day stimulation. β-ManCer and α-GalCer induced similar proliferation of the different Vβ subsets of iNKT cells (FIG. 4). Vβ2$^+$ iNKT cells had the highest background proliferation, but no additional proliferation was observed after stimulation. An unexplained decrease in proliferation of the Vβ subset after antigen stimulation was consistently observed. Vβ8$^+$ iNKT cells proliferated the most, followed by Vβ7$^+$ iNKT cells. This suggests that β-ManCer stimulates NKT cells with a similar Vβ repertoire as α-GalCer.

Figure 5:
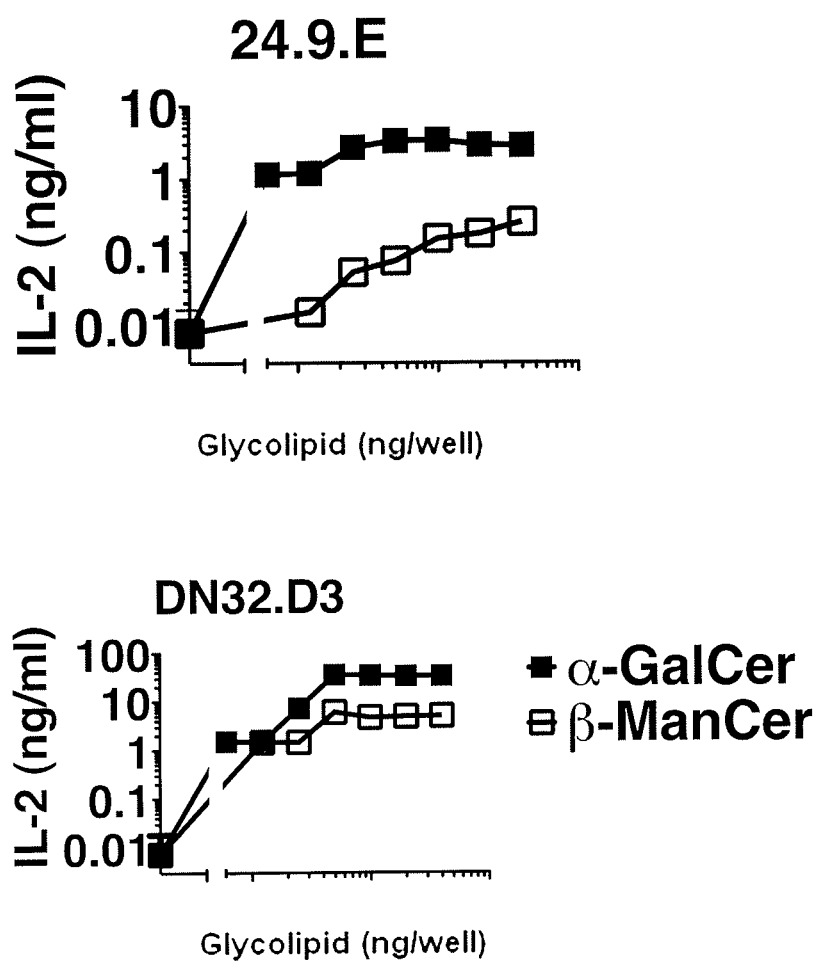
FIG. 5 shows two graphs depicting that β-ManCer loaded dimers were able to induce IL-2 production by both the 24.9.E and DN32.D3 NKT cell lines. Unloaded CD1d (0 ng/well) or soluble β-ManCer in the absence of CD1d failed to induce IL-2 production above background.

In order to further demonstrate that β-ManCer directly activates iNKT cells, the ability of β-ManCer to stimulate the 24.9.E and DN32.D3 NKT cell hybridomas, which express the iNKT cell TCR Vα14Jα18 (33, 34) was tested. In this system, β-ManCer or α-GalCer were loaded onto mouse CD1d (mCD1d) dimers, which were coated onto 96-well plates in the absence of any additional cell types, including APCs. β-ManCer loaded dimers were able to induce IL-2 production by both the 24.9.E and DN32.D3 NKT cell lines. Unloaded CD (0 ng/well) or soluble β-ManCer in the absence of CD failed to induce IL-2 production above background (FIG. 5). While β-ManCer induces less IL-2 production than α-GalCer (10- to 50-fold difference), this is not surprising, since almost all assays comparing α-GalCer and β-ManCer demonstrate that β-ManCer is not as potent a stimulator of iNKT cells as α-GalCer. However, the increase in IL-2 production after β-ManCer stimulation is 25-, and over 500-fold higher, than that induced by unloaded mCD1d for the 24.9.E and DN32.D3 hybridomas, respectively, indicating a substantial and unequivocal increase in IL-2 production. These findings demonstrate that β-ManCer, presented by CD1d, directly activates iNKT cells in the absence of any other cells.

Figure 6:
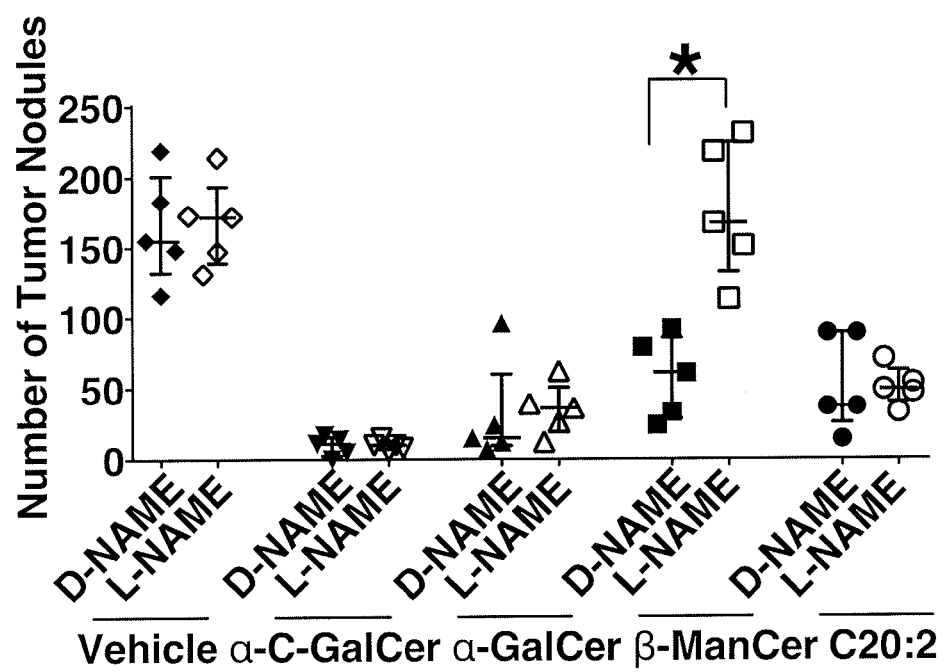
FIG. 6 is a graph showing that at the 50 pmole dose, mice treated with α-C-GalCer and α-GalCer developed a similar number of lung nodules. NOS inhibition had no effect on the activity of α-C-GalCer against lung tumors, similar to the results obtained with the other α-GalCer analogs. (*, statistically significant from vehicle control, p<0.05)

Previously, it has been reported that α-C-GalCer, the C-glycoside analog of α-GalCer in which a $CH_2$ group replaces the glycosidic oxygen, is more potent than α-GalCer against lung metastasis in the B16 melanoma transplantable tumor model. This analog induces a cytokine response more skewed toward Th1 cytokines than does 13-GalCer due to markedly reduced production of Th2 cytokines. Because α-C-GalCer and α-GalCer have been classified differently based on the cytokine profile they induce and the mechanism of induction, a determination of whether α-C-GalCer induced antitumor immunity through a mechanism similar to that of β-ManCer was undertaken. At the 50 pmole dose, mice treated with α-C-GalCer and α-GalCer developed a similar number of lung nodules. NOS inhibition had no effect on the activity of α-C-GalCer against lung tumors, similar to the results obtained with the other α-GalCer analogs (FIG. 6). These findings indicate that β-ManCer does not fit into any of the previous classifications of iNKT agonists.

Example 3

In this example a comparison of cytokine production is undertaken to determine whether the tumor inhibition of β-ManCer is due to cytokine production.

In order to identify potential correlates of tumor protection, the cytokine production induced by the glycolipid panel was characterized. In vitro, α-GalCer induced the greatest IFN-γ production, while C20:2, OCH, and AH04-2 induced a Th2-skewed cytokine profile with a lower IFN-γ level (FIG. 7A) and higher amounts of IL-4 (FIG. 7B) and IL-13 (FIG. 7C). β-ManCer also induced the least cytokine production, with no cytokines detected at concentrations less than 30 nM.

Figure 8:
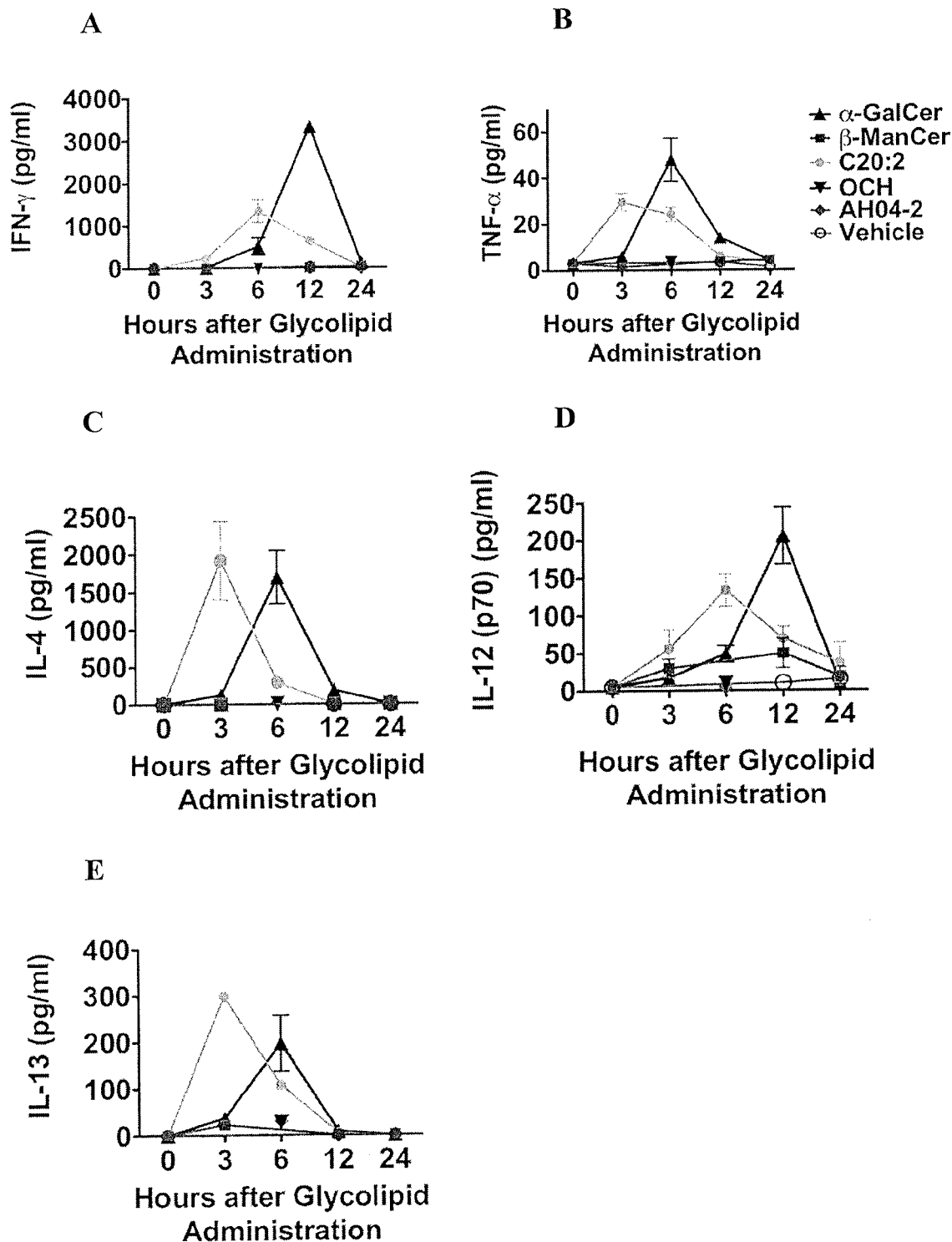

Similar to the in vitro results, α-GalCer induced the most IFN-γ in vivo, followed by C20:2 (FIG. 8A). It was found that C20:2 produced a cytokine profile more skewed toward Th2, with increased IL-4 (FIG. 8C) and IL-13 (FIG. 8E) production, and that C20:2 and α-GalCer induced similar levels of IL-12 (FIG. 8B) and TNF-α (FIG. 8D). Much less cytokine production was detected following OCH and AH04-2 administration, which was consistent with these compounds' lack of significant protection at this dose. The absence of detectable cytokine production following in vitro stimulation with β-ManCer was also confirmed in vivo, as there was no substantial increase in IFN-γ, IL-4, or IL-13 levels following treatment with 50 pmoles β-ManCer, and only a modest increase in IL-12 or TNF-α. It was determined that for the α-galactosyl glycolipids tested, the amount of IFN-γ correlated with tumor protection. However, and more importantly, β-ManCer is a potent stimulator of anti-tumor immunity despite its failure to induce meaningful levels of IFN-γ, IL-4, IL-13, or TNF-α in the blood.

Example 4

In this example, β-ManCer-induced protection is tested in IFN-γ knockout mice to determine whether β-ManCer-induced protection is dependent upon IFN-γ.

iNKT cell-mediated anti-tumor immunity is thought to be the result of IFN-γ production by activated iNKT cells. While α-GalCer and C20:2 completely failed to induce any tumor protection in IFN-γ knockout mice, β-ManCer treatment surprisingly still resulted in 50% fewer lung nodules compared to vehicle control mice (p=0.0079) (FIG. 9A). In contrast to the α-galactosylceramides, α-GalCer and C20:2, whose protection is completely dependent on IFN-γ, β-ManCer was able to induce protection even though it has a substantial IFN-γ-independent component.

In order to further investigate the mechanism(s) by which these glycolipids induce tumor protection, the involvement of effector cells which can lead to tumor cell lysis was examined. Depletion of CD8+ cells had no effect on the number of lung nodules compared with mice treated with control antibody (FIG. 9B). Depletion of NK cells with anti-asialo GM1 antibody resulted in a slight increase in tumor nodules, which was similar in all groups, including vehicle-treated mice (FIG. 9C). Thus, the ability of these glycolipids to prevent tumor formation is not dependent on CD8+ T cells and largely independent of NK cells.

Example 5

The purpose of this example is to demonstrate that β-ManCer-induced tumor elimination is NOS and TNF-α-dependent.

Having ruled out CD8+ T cells and NK cells as the major mediators of protection, the role of nitric oxide, by which macrophages may protect against tumors, was examined. Mice were treated with L-NAME, which inhibits nitric oxide synthase (NOS) in vivo. NOS inhibition had no effect on tumor formation in vehicle-, α-GalCer-, or C20:2-treated mice, as there was no difference between mice treated with L-NAME, or its inactive enantiomer, D-NAME (FIG. 10A). However, administration of L-NAME significantly inhibited protection induced by β-ManCer (p=0.0027) such that there was no significant difference from vehicle-treated mice. NOS inhibition also failed to affect protection by α-C-GalCer, the C-glycoside analog of α-GalCer, which induces a cytokine profile even more skewed toward IFN-γ. These data also suggest distinct mechanisms of tumor protection between β-ManCer and the α-galactosylceramides.

The data show that blockade of NOS, but not knockout of IFN-γ. completely reversed β-ManCer-induced protection. A study was then performed to determine whether the protection induced by β-ManCer in IFN-γ−/− mice could also be reversed by inhibiting NOS. Indeed, it was found that protection induced by β-ManCer was completely lost in IFN-γ−/− mice when NOS was inhibited (FIG. 10B), suggesting an IFN-γ independent mechanism for NOS induction. Because NOS can also be induced by TNF-α, a separate study was undertaken to determine whether β-ManCer was inducing NOS through TNF-α. Again, it was found that blockade of TNF-α by soluble TNF-αR-Fc fusion protein completely reversed the protection induced by β-ManCer, but had no effect on protection induced by α-GalCer (FIG. 10C). Taken together, these data suggest that β-ManCer and α-GalCer induce tumor immunity through distinct mechanisms.

It has been reported that CD11b+Gr-1+ cells produce nitric oxide and are involved in NKT cell-mediated graft loss in transplantation. It was found that depletion of Gr-1+ cells had no effect on the tumor protection induced by β-ManCer (FIG. 10D), suggesting that Gr-1+ cells neither are the critical nitric oxide producing cells, nor are they required for this protection.

Example 6

Due to the evidence that the effects of α-GalCer and β-ManCer appear to operate via different cellular mechanisms, the purpose of the following example is to determine whether simultaneous treatment with α-GalCer and β-ManCer induces synergistic anti-tumor activity.

This study provides multiple lines of evidence that β-ManCer and the α-glycosylceramides induce tumor protection through distinct mechanisms. Thus, it was hypothesized that simultaneous treatment with these glycolipids may act synergistically. To address this hypothesis, mice were treated with sub-therapeutic doses of each glycolipid separately, as well as in combination. The combination of these two antigens at these sub-therapeutic doses resulted in a 79% reduction of the median number of tumor nodules (p=0.0119), suggesting that α-GalCer and β-ManCer work synergistically to eliminate/prevent CT26 lung metastases, and confirming the conclusion that these two antigens induce iNKT cell-mediated protection through distinct mechanisms (FIG. 11). We conclude that β-ManCer represents a new class of NKT-cell agonists not previously known, and the first beta-linked glycosylceramide to show significant protective activity against cancers.

Example 7

This example demonstrates that β-ManCer can also induce protection against cancers other than CT26 colon cancer, including melanoma.

The ability of α-GalCer and β-ManCer to protect against a different type of cancer, for example, B16F10 melanoma lung metastasis, was tested in C57BL/6 mice by titrating both in vivo. It was found that β-ManCer was at least as potent an inducer of tumor protection as α-GalCer in this model (FIG. 12). This study also shows that β-ManCer is effective in more than one strain of mice.

Example 8

One of the inherent problems with cancer immunotherapy is the induction of anergy after repeated treatment. This example demonstrates that due to its unique mechanism of action, β-ManCer does not induce strong anergy of activated NKT cells.

It is known that α-GalCer induces strong anergy of activated NKT cells for over a month after in vivo stimulation. Because β-ManCer does not induce large amounts of cytokine production, it was hypothesized that it might not induce anergy. Mice were treated with α-GalCer, β-ManCer, or vehicle, and one month later, splenocytes were re-stimulated, and the degree of activation was measured by proliferation and IFN-γ production. The ability of cells from α-GalCer-treated mice to respond to re-stimulation by either α-GalCer or 13-ManCer was severely suppressed when compared to cells from vehicle-treated mice (FIGS. 13A and 13B). Interestingly, while there was a slight reduction in proliferation and IFN-γ production following re-stimulation of cells from β-ManCer-treated mice, a significant response was still observed, suggesting that unlike α-GalCer, β-ManCer, does not induce strong anergy of activated NKT cells.

Example 9

This example demonstrates that β-ManCer activates human iNKT cells. An experiment was performed to give an initial determination of whether β-ManCer could activate human iNKT cells. Human PBMCs were stimulated with β-ManCer or α-GalCer for 4 days. iNKT cells were defined as Vα24+CD3$^{intermediate}$PBS57/CD1d tetramer+ (FIG. 14A), and proliferation was measured by dilution of Cell-Trace Violet Dye. β-ManCer induced proliferation of human iNKT cells similar to that induced by α-GalCer (FIG. 14B). These results suggest that β-ManCer has the potential for use in human patients.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising a β-mannosylceramide (β-ManCer) or salt or solvate thereof in a pharmaceutically acceptable carrier, wherein the β-ManCer consists of:

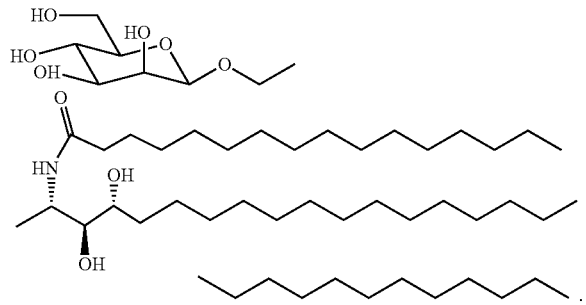

2. The composition of claim 1 further comprising a therapeutically effective amount of IL-2.

3. The composition of claim 1 further comprising a therapeutically effective amount of an α-glucosylceramide or a salt or solvate thereof.

4. The composition of claim 1 further comprising GM-CSF and/or one or more cytokines that induce cellular immunity.

5. The composition claim 4, wherein the one or more cytokines that induce cellular immunity comprises IL-12 and/or IL-15.

6. The composition of claim 1 further comprising at least one T-cell co-stimulatory molecule selected from the group consisting of B7-1, B7-2, B7-3, 87-H, ICAM1, ICAM2, ICAM3, LFA1, LFA2, LFA3, CD40L, OX40L and 4-1BBL.

7. The composition of claim 1 further comprising at least one Toll-like Receptor (TLR) ligand.

8. The composition of claim 7, wherein the at least one TLR ligand is a ligand for a molecule selected from the group consisting of TLR2, TLR3, TLR4, TLR5, TLR7, TLR8, and TLR9.

9. The composition of claim 1 further comprising a vaccine.

10. The composition of claim 9, wherein the vaccine is selected from the group consisting of TARP 29-37-9V peptide and Sargramostin (GM-CSF) emulsified in Montanide ISA 51 VG.

11. The composition of claim 1 further comprising an antibody.

12. The composition of claim 11, wherein the antibody is against a molecule selected from the group consisting of CTLA-4, PD-1, and TGF-β.

13. A method for activating a mammalian NKT cell in vitro, the method comprising:
    culturing in vitro a mononuclear cell fraction comprising one or more mammalian NKT cells in the presence of a composition in an amount sufficient to activate a mammalian NKT cell in vitro without increasing interleukin (IL)-4,
    wherein the composition comprises a β-mannosylceramide (β-ManCer) or salt or solvate thereof in a pharmaceutically acceptable carrier, wherein the β-ManCer consists of:
    a) a sphingosine moiety; and
    b) a fatty acid moiety comprising a linear or branched, saturated or unsaturated, aliphatic hydrocarbon group having from about 8 to about 49 carbon atoms.

14. A method of inducing an immune response, treating cancer, or inhibiting growth of a tumor in a subject, the method comprising
administering to the subject a composition in an amount effective to induce an immune response, treat cancer, or inhibit growth of a tumor in the subject without increasing interleukin (IL)-4 in the subject,
wherein the composition comprises a β-mannosylceramide (β-ManCer) or salt or solvate thereof in a pharmaceutically acceptable carrier, wherein the β-ManCer consists of:
a) a sphingosine moiety; and
b) a fatty acid moiety comprising a linear or branched, saturated or unsaturated, aliphatic hydrocarbon group having from about 8 to about 49 carbon atoms, and
wherein the cancer is selected from the group consisting of lung cancer, colon cancer, and melanoma and the tumor is selected from the group consisting of a lung tumor, a colon tumor, and a melanoma tumor.

15. The method of claim 14, wherein the composition further comprises a therapeutically effective amount of one or more chemotherapeutic agents.

16. A method of treating cancer or inhibiting growth of a tumor in a subject, the method comprising
culturing in vitro a mononuclear cell fraction comprising one or more mammalian NKT cells in the presence of a composition in an amount sufficient to activate a mammalian NKT cell in vitro without increasing interleukin (IL)-4,
administering the activated mammalian NKT cells to the subject in an amount effective to treat cancer or inhibit growth of a tumor in the subject,
wherein the composition comprises β-mannosylceramide (β-ManCer) or salt or solvate thereof in a pharmaceutically acceptable carrier, wherein the β-ManCer consists of:
a) a sphingosine moiety; and
b) a fatty acid moiety comprising a linear or branched, saturated or unsaturated, aliphatic hydrocarbon group having from about 8 to about 49 carbon atoms, and
wherein the cancer is selected from the group consisting of lung cancer, colon cancer, and melanoma and the tumor is selected from the group consisting of a lung tumor, a colon tumor, and a melanoma tumor.

17. The method of claim 16, wherein the activated mammalian NKT cells are autologous to the subject being treated.

18. The composition of claim 3, wherein the α-glycosylceramide has the following structure:

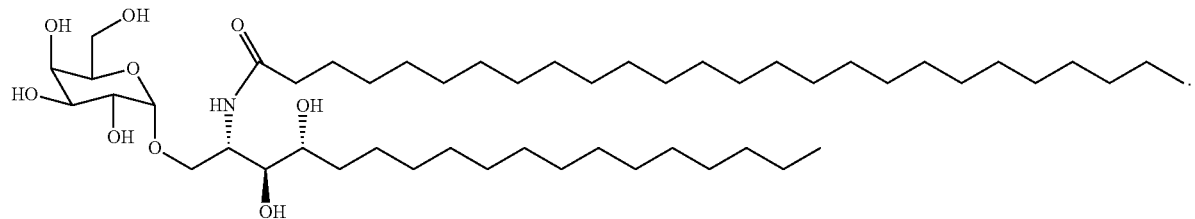 [SMILES: CCCCCCCCCCCCCCCCCCCCCCCCCC(=O)N[C@@H](COC1OC(CO)C(O)C(O)C1O)[C@H](O)[C@H](O)CCCCCCCCCCCCCC]

19. The method of treating cancer or inhibiting growth of a tumor of claim 14, wherein the cancer is colon cancer and the tumor is a lung tumor.

20. A method of treating cancer or inhibiting growth of a tumor in a subject, the method comprising administering to the subject the composition of claim 18 in an amount effective to treat cancer or inhibit growth of a tumor in the subject, wherein the cancer or tumor is colon cancer or colon cancer lung metastasis.

21. A method for activating a mammalian NKT cell in vitro comprising: culturing in vitro a mononuclear cell fraction comprising one or more mammalian NKT cells in the presence of the composition of claim 18 in an amount sufficient to activate a mammalian NKT cell in vitro.

22. The method of claim 13, wherein the β-ManCer consists of the following structure:

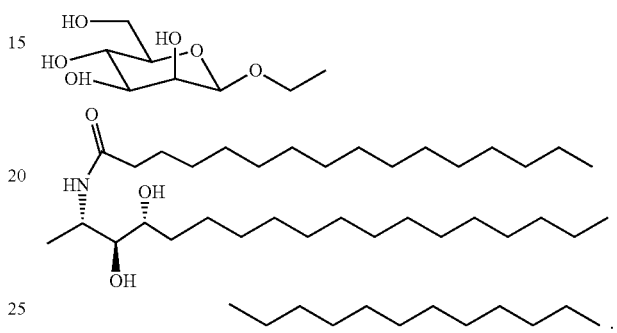

23. The method of claim 14, wherein the β-ManCer consists of the following structure:

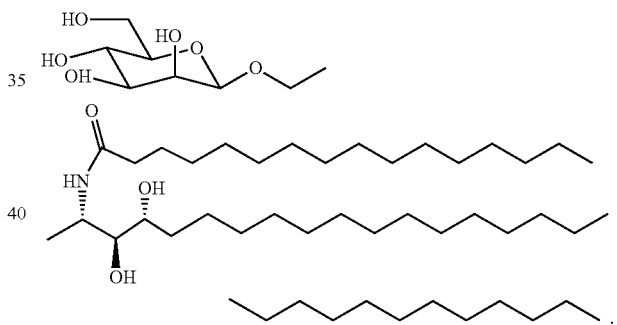

24. The method of claim 16, wherein the β-ManCer consists of the following structure:

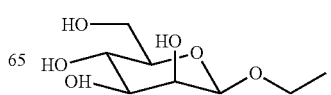

-continued
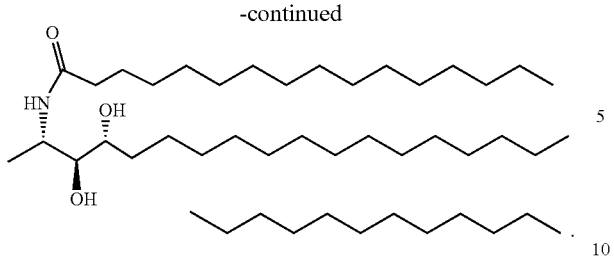
* * * * *